US009029786B2

(12) United States Patent
Moriyasu et al.

(10) Patent No.: US 9,029,786 B2
(45) Date of Patent: May 12, 2015

(54) NUCLEAR MEDICINE IMAGING APPARATUS, AND NUCLEAR MEDICINE IMAGING METHOD

(75) Inventors: Kenta Moriyasu, Nasushiobara (JP); Nobutoku Motomura, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/161,904

(22) Filed: Jun. 16, 2011

(65) Prior Publication Data
US 2011/0309252 A1 Dec. 22, 2011

(30) Foreign Application Priority Data

Jun. 17, 2010 (JP) .................................. 2010-138462
Jun. 17, 2010 (JP) .................................. 2010-138463

(51) Int. Cl.
*G01T 1/164* (2006.01)
*A61B 6/00* (2006.01)
(Continued)

(52) U.S. Cl.
CPC .............. *A61B 6/585* (2013.01); *G01T 1/2985* (2013.01); *G01T 1/1644* (2013.01); *A61B 6/037* (2013.01); *A61B 6/4266* (2013.01); *G01T 7/005* (2013.01)

(58) Field of Classification Search
CPC ...... G01T 1/2985; G01T 1/1644; G01T 7/005
USPC .......................................... 250/363.03, 252.1
See application file for complete search history.

(56) References Cited

U.S. PATENT DOCUMENTS 4,873,632 A * 10/1989 Logan et al. ............. 250/363.02
5,272,344 A * 12/1993 Williams ................. 250/363.03
(Continued)

FOREIGN PATENT DOCUMENTS

CN 101111781 A 1/2008
JP 58-6499 1/1983
(Continued)

OTHER PUBLICATIONS

A.E. Perkins, et al., "Time of Flight Coincidence Timing Calibration Techniques Using Radioactive Sources," 2005, IEEE Nuclear Science Symposium Conference Record, 4 pages.
(Continued)

*Primary Examiner* — David Porta
*Assistant Examiner* — Jeremy S Valentiner
(74) *Attorney, Agent, or Firm* — Oblon, McClelland, Maier & Neustadt, L.L.P.

(57) ABSTRACT

According to one embodiment, a nuclear medicine imaging apparatus includes a detector, a calibrator, and an image reconstruction unit. The detector includes a plurality of detector modules, each counting light originating from a gamma ray. The calibrator unit calibrates time information of all of the plurality of detector modules by calibrating time information for determining each detection time of a pair of detector modules based on each detection time of the pair of the detector modules which approximately coincidentally count annihilation gamma rays and a distance between the pair of detector modules in a state in which a point radiation source including a positron emitting nuclide is installed in each position near a plurality of predetermined detector modules. The image reconstruction unit reconstructs a nuclear medicine image using a time difference between detection times of annihilation gamma rays corrected based on time information calibrated by the calibrator.

19 Claims, 17 Drawing Sheets

(51) Int. Cl.
*G01T 1/29* (2006.01)
*A61B 6/03* (2006.01)
*G01T 7/00* (2006.01)

(56) References Cited

U.S. PATENT DOCUMENTS

| | | | |
|---|---|---|---|
| 5,703,369 A * | 12/1997 | Mori | 250/363.03 |
| 6,072,177 A * | 6/2000 | McCroskey et al. | 250/252.1 |
| 6,329,657 B1 * | 12/2001 | Watson et al. | 250/363.04 |
| 6,774,358 B2 * | 8/2004 | Hamill et al. | 250/252.1 |
| 2003/0189174 A1 * | 10/2003 | Tanaka et al. | 250/363.03 |
| 2004/0075048 A1 | 4/2004 | Zyromski | |
| 2004/0251419 A1 * | 12/2004 | Nelson et al. | 250/370.09 |
| 2005/0156112 A1 * | 7/2005 | Williams et al. | 250/363.03 |
| 2006/0102845 A1 * | 5/2006 | Williams et al. | 250/363.03 |
| 2007/0131857 A1 * | 6/2007 | Thompson et al. | 250/252.1 |
| 2007/0152162 A1 | 7/2007 | Griesmer et al. | |
| 2008/0130838 A1 * | 6/2008 | Muehllehner et al. | 378/207 |
| 2010/0059682 A1 | 3/2010 | Conti | |
| 2012/0049053 A1 * | 3/2012 | Olivier et al. | 250/252.1 |

FOREIGN PATENT DOCUMENTS

| | | |
|---|---|---|
| JP | 2007-107995 | 4/2007 |
| JP | 2008-528996 A | 7/2008 |
| JP | 2010-91391 A | 4/2010 |

OTHER PUBLICATIONS

Chinese Office Action issued Mar. 5, 2013 in Patent Application No. 201110162952.X with English Translation of Category of Cited Documents.

Office Action issued on Jun. 17, 2014 in the corresponding Japanese Patent Application No. 2010-138463 (with English Translation).

Office Action issued Dec. 24, 2014 in Japanese Patent Application No. 2011-129464.

Office Action issued Jan. 13, 2015 in Japanese Patent Application No. 2010-138463.

Tomoyuki Hasegawa, et al., "Evaluation and Calibration of PET Scanners with a Specially Designed Point-like Radioactive Source", IEEE Nuclear Science Symposium Conference Record, 2009, pp. 3630-3632.

* cited by examiner

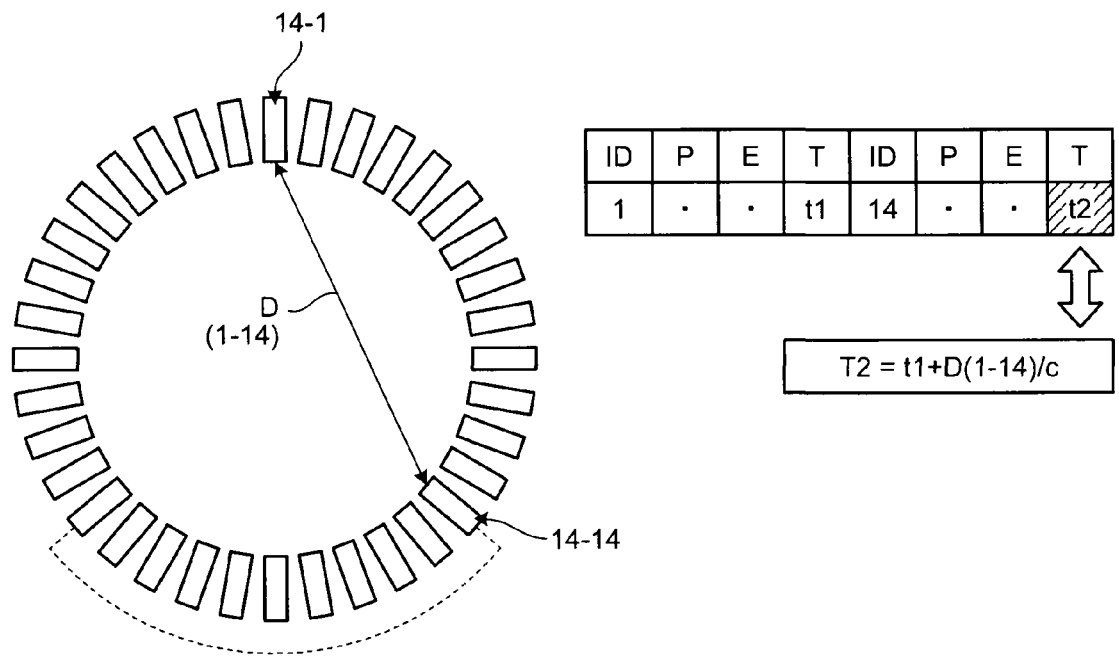

| P | E | T | P | E | T |
|---|---|---|---|---|---|
| P1_1 | E1_1 | T1_1 | P2_2 | E2_2 | T2_2 |
| P10_2 | E10_2 | T10_2 | P3_2 | E3_2 | T3_2 |
| P8_3 | E8_3 | T8_3 | P20_3 | E20_3 | T20_3 |
| ⋮ | ⋮ | ⋮ | ⋮ | ⋮ | ⋮ |

| P | E | T | P | E | T |
|---|---|---|---|---|---|
| P1_1 | E1_1 | T1_1 | P2_2 | E2_2 | T2_2+$\Delta t2$ |
| P10_2 | E10_2 | T10_2+$\Delta t10$ | P3_2 | E3_2 | T3_2+$\Delta t3$ |
| P8_3 | E8_3 | T8_3+$\Delta t8$ | P20_3 | E20_3 | T20_3+$\Delta t20$ |
| ⋮ | ⋮ | ⋮ | ⋮ | ⋮ | ⋮ |

FIG.16
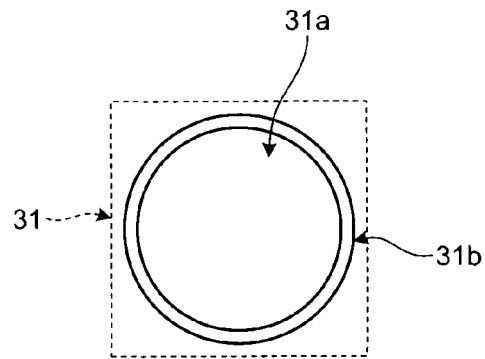
FIG.17
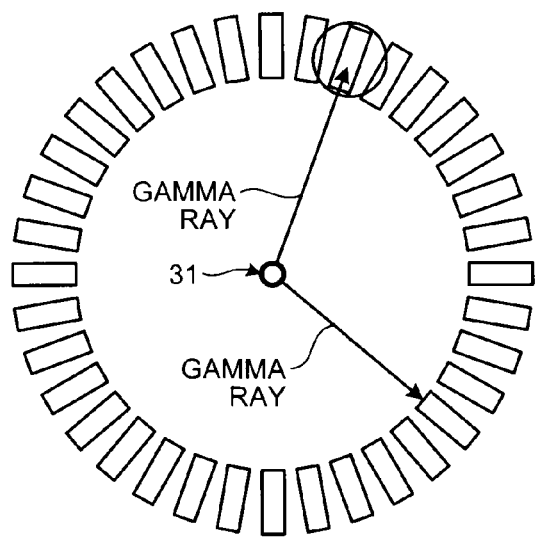
FIG.18
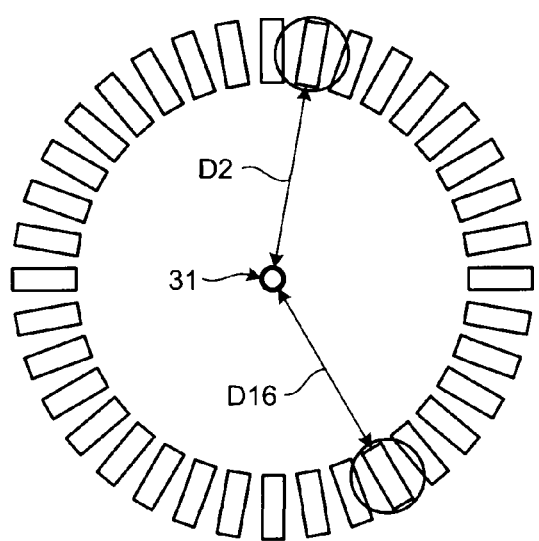
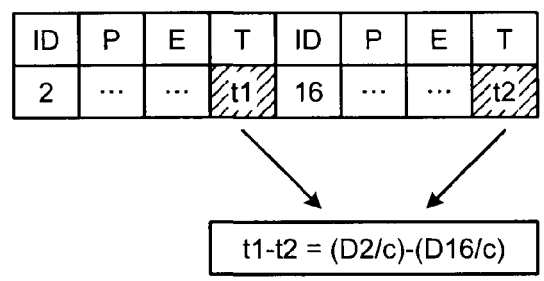

FIG.19

| ID | TIME INFORMATION |
|---|---|
| 1 | 0 |
| 2 | $\Delta t2$ |
| 3 | $\Delta t3$ |
| 4 | $\Delta t4$ |
| 5 | $\Delta t5$ |
| 6 | $\Delta t6$ |
| 7 | $\Delta t7$ |
| 8 | $\Delta t8$ |
| 9 | $\Delta t9$ |
| 10 | $\Delta t10$ |
| ⋮ | ⋮ |

| P | E | T | P | E | T |
|---|---|---|---|---|---|
| P1_1 | E1_1 | T1_1 | P2_2 | E2_2 | T2_2 |
| P10_2 | E10_2 | T10_2 | P3_2 | E3_2 | T3_2 |
| P8_3 | E8_3 | T8_3 | P20_3 | E20_3 | T20_3 |
| ⋮ | ⋮ | ⋮ | ⋮ | ⋮ | ⋮ |

| P | E | T | P | E | T |
|---|---|---|---|---|---|
| P1_1 | E1_1 | T1_1 | P2_2 | E2_2 | T2_2+$\Delta$t2 |
| P10_2 | E10_2 | T10_2+$\Delta$t10 | P3_2 | E3_2 | T3_2+$\Delta$t3 |
| P8_3 | E8_3 | T8_3+$\Delta$t8 | P20_3 | E20_3 | T20_3+$\Delta$t20 |
| ⋮ | ⋮ | ⋮ | ⋮ | ⋮ | ⋮ |

NUCLEAR MEDICINE IMAGING APPARATUS, AND NUCLEAR MEDICINE IMAGING METHOD

CROSS-REFERENCE TO RELATED APPLICATIONS

This application is based upon and claims the benefit of priority from Japanese Patent Application No. 2010-138462, filed on Jun. 17, 2010; and Japanese Patent Application No. 2010-138463, filed on Jun. 17, 2010, the entire contents of all of which are incorporated herein by reference.

FIELD

Embodiments described herein relate generally to a nuclear medicine imaging apparatus and a nuclear medicine imaging method.

BACKGROUND

In the related art, a positron emission computed tomography (PET) apparatus has been known as a nuclear medicine imaging apparatus capable of performing functional diagnosis in body tissues of a subject.

Specifically, in a PET examination, a medical agent labeled by a positron emitting nuclide is introduced into a subject. In addition, the PET apparatus coincidentally counts a pair of gamma rays (annihilation gamma rays) of 511 keV emitted in the nearly opposite direction, when positrons emitted from the medical agent combine with electrons so as to be annihilated, using a detector composed of photon counting type detector modules arranged in a ring shape around the subject. In addition, the PET apparatus reconstructs a PET image by operating data of the coincidentally counted gamma rays (coincidence count information).

In recent years, a time-of-flight (TOF)-PET apparatus for precisely specifying the location where the gamma ray is emitted using the time difference between detection times of the annihilation gamma rays has been developed. Since the gamma ray propagates at a light velocity, the detection time difference required in the TOF-PET apparatus is about several hundreds of picoseconds. For this reason, in the TOF-PET apparatus, it is necessary to adjust the time information for determining the detection time of each detector module with high precision.

As a method of calibrating time information of each detector module, a technique using a point radiation source such as germanium-68 is typically used. In such a technique, the point radiation source is installed within a field of view (FOV) of the PET image, and the annihilation gamma rays generated from the point radiation source are detected by a pair of detector modules. In such a technique, the time information is calibrated using the detection time of a pair of detector modules detecting the annihilation gamma ray.

However, in the calibration method described above, a combination of two detector modules detecting the annihilation gamma rays is limited to a straight line shape passing through the point radiation source. Therefore, in the calibration technique described above, it is difficult to calibrate the time information of all detector modules.

BRIEF DESCRIPTION OF THE DRAWINGS

FIG. 9 is a diagram illustrating a calibrator according to the first embodiment;
FIG. 10 is a diagram illustrating time information data according to the first embodiment;
FIG. 16 is a diagram illustrating a point radiation source used in a second embodiment;
FIG. 17 is a diagram illustrating a combination of detector modules capable of detecting annihilation gamma rays according to the second embodiment;
FIG. 18 is a diagram illustrating a calibrator according to the second embodiment;
FIG. 19 is a diagram illustrating time information data according to the second embodiment.

DETAILED DESCRIPTION

According to one embodiment, a nuclear medicine imaging apparatus includes a detector, a calibrator, and an image reconstruction unit. The detector includes a plurality of detector modules, each counting light originating from a gamma ray. The calibrator is configured to calibrate time information of all of the plurality of detector modules by calibrating time information for determining each detection time of a pair of detector modules based on each detection time of the pair of the detector modules which approximately coincidentally count annihilation gamma rays and a distance between the pair of detector modules in a state in which a point radiation source including a positron emitting nuclide is installed in each position near a plurality of predetermined detector modules. The image reconstruction unit is configured to reconstruct a nuclear medicine image of a subject using a time difference between detection times of annihilation gamma rays corrected based on time information of each of the plurality of detector modules calibrated by the calibrator when the subject into which a substance labeled with a positron emitting nuclide is introduced is scanned.

Hereinafter, a positron emission computed tomography (PET) apparatus as a nuclear medicine imaging apparatus according to embodiments will be described.

The PET apparatus is an apparatus for reconstructing PET images representing the distribution of tissues that receive positron emitting nuclides by coincidentally counting each pair of gamma rays (annihilation gamma rays) emitted from the tissues that receive the positron emitting nuclides introduced into a subject. Here, the PET apparatus according to the present embodiment is an apparatus for reconstructing time-of-flight (TOF) PET images using a TOF technique in which a gamma ray emission position is precisely specified using the detection time difference of the annihilation gamma ray.

Figure 1:
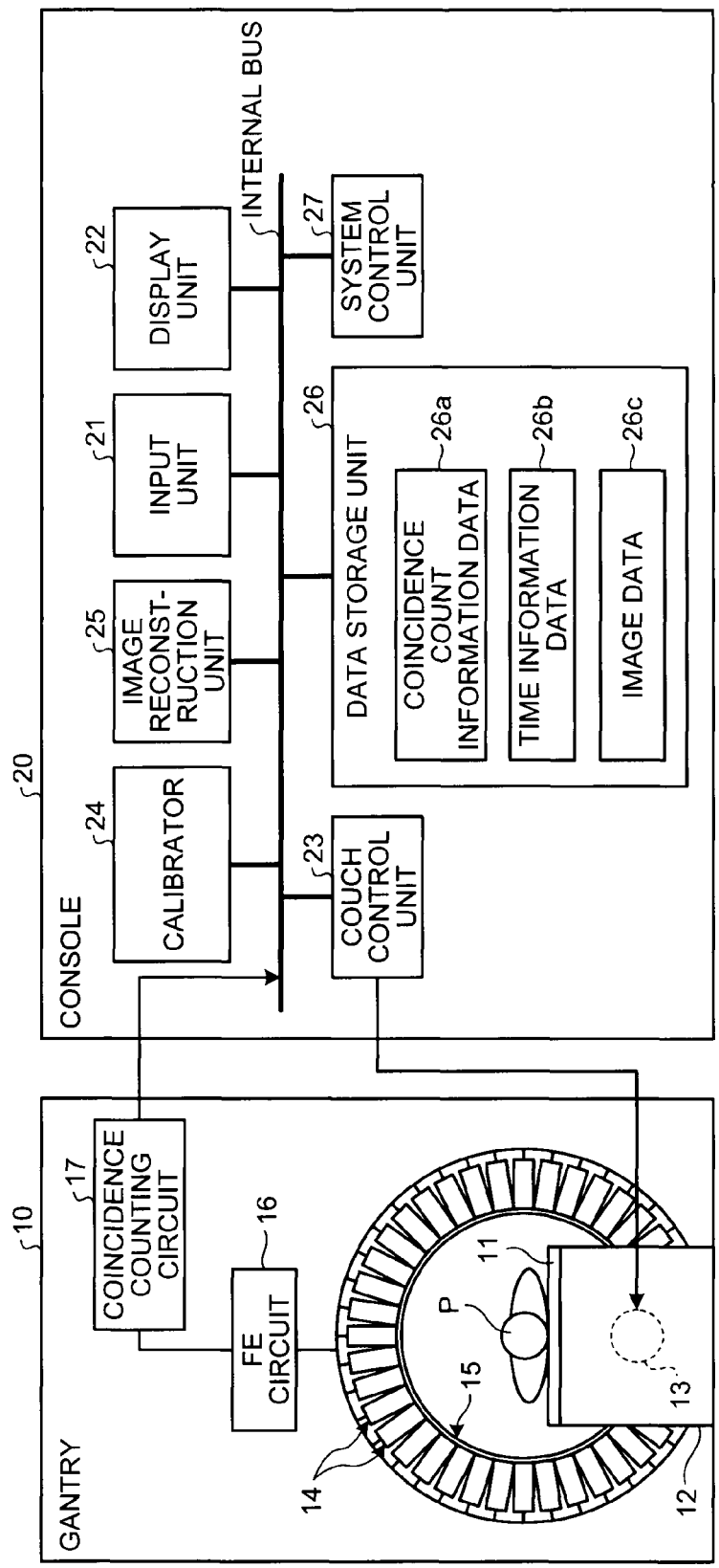
FIG. 1 is a diagram illustrating a configuration of a PET apparatus according to a first embodiment.

First, a configuration of a PET apparatus according to a first embodiment will be described with reference to FIG. 1. FIG. 1 is a diagram illustrating the configuration of the PET apparatus according to the first embodiment. As shown in FIG. 1, the PET apparatus according to the first embodiment includes a gantry 10 and a console 20.

The gantry 10 is an apparatus for counting the annihilation gamma rays emitted from the positron emitting nuclide introduced into a subject P and selectively received by the body tissues of the subject P for a predetermine monitoring time period. The gantry 10 includes a top board 11, a couch 12, a couch drive unit 13, a detector module 14, a detector cover 15, an FE circuit 16, and a coincidence counting circuit 17. In addition, the gantry 10 has a cavity serving as a scanning bore as shown in FIG. 1.

The top board 11 is a bed where the subject P is laid and is arranged on the top of the couch 12. The couch drive unit 13 moves the subject P into the scanning bore of the gantry 10 by moving the couch 12 under control of a couch control unit 23 to be described below.

Figure 2:
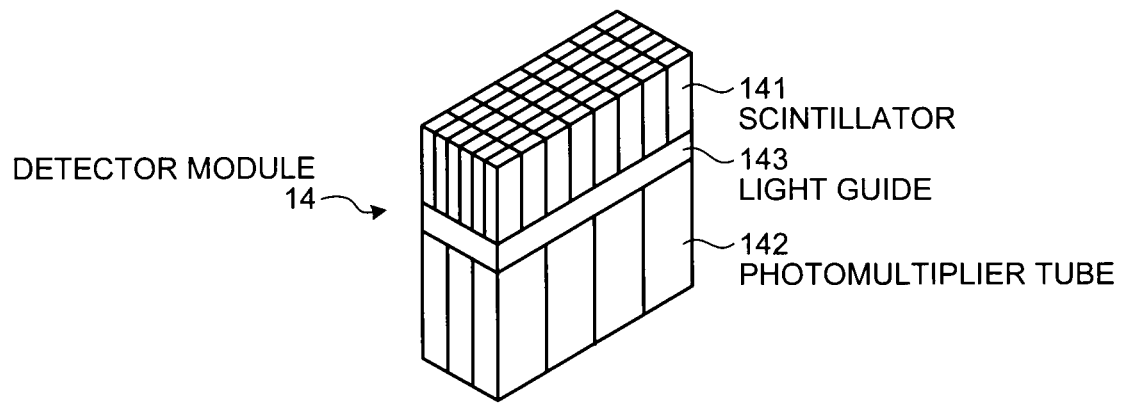
FIG. 2 is a diagram illustrating a detector module.

The detector module 14 counts the light originating from the gamma ray. That is, the detector module 14 is a photon counting type detector module 14 in which the gamma ray emitted from the subject P is detected. For example, in the gantry 10, a plurality of detector modules 14 are arranged to surround the subject P in a ring shape. In addition, the arrangement of a plurality of detector modules 14 is not limited to the ring shape. For example, two of a plurality of detector modules 14 arranged on a flat board may be disposed on opposite sides of the subject P. Hereinafter, a plurality of detector modules 14 may be collectively referred to as a detector in brief. That is, the detector includes a plurality of detector modules 14. FIG. 2 is a diagram illustrating the detector module.

For example, as shown in FIG. 2, the detector module is an anger type detector including a scintillator 141, a photomultiplier tube (PMT) 142, and a light guide 143.

In the scintillator 141, crystals of sodium iodide (NaI) or bismuth germanate (BGO) convert incident the gamma ray emitted from the subject P into visible light and are two dimensionally arranged as shown in FIG. 2. In addition, the photomultiplier tube 142 is an apparatus that multiplies the visible light outputted from the scintillator 141 and converts the visible light into an electric signal. As shown in FIG. 2, a plurality of photomultiplier tubes 142 are densely arranged by interposing the light guides 143. The light guide 143 is used to transmit the visible light output from the scintillator 141 to the photomultiplier tube 142 and is made of a plastic material or the like having high light transmittance.

The photomultiplier tube 142 includes a photocathode that receives the scintillation light and generates photoelectrons, a multi-stage dynode that generates an electric field for accelerating the generated photoelectrons, and an anode which is an outlet through which electrons flow out. The electron emitted from the photocathode by the photoelectric effect is accelerated toward the dynode and collides with the surface of the dynode, resulting in a plurality of electrons escaping. If such a phenomenon is repeated over the multi-stage dynode, the number of electrons increases by geometrical progression, so that the number of electrons at the anode finally reaches about 1,000,000. In such an example, the gain of the photomultiplier tube 142 is about 1,000,000. In addition, typically, a voltage of 600 V or higher is applied between the dynode and the anode in order to perform amplification using the avalanche phenomenon.

As such, the detector module 14 counts the number of gamma rays emitted from the subject P by converting the gamma rays into visible light using the scintillator 141 and converting the converted visible light into the electric signal using the photomultiplier tube 142.

Returning to FIG. 1, the detector cover 15 is used to encase the detector including the plurality of detector modules 14. In addition, each detector module 14 is encased in a module cover, and the detector cover 15 encases the detector modules 14 each being encased in the module cover.

The FE circuit 16 is connected to the rear end of the photomultiplier tube 142 of each of the plurality of detector modules 14 and to the front end of the coincidence counting circuit 17. The FE circuit 16 generates various kinds of data used in processing performed by the coincidence counting circuit 17 on the basis of the electric signals output from each photomultiplier tube 142.

That is, the FE circuit 16 carries out a waveform shaping process with respect to analog waveform data of the electric signals output from each photomultiplier tube 142. Specifically, the FE circuit 16 carries out an operational process (integration and differentiation) with respect to the analog waveform data to create data in which the wave height corresponds to the energy.

In addition, the FE circuit 16 determines an incident position of the gamma ray. Specifically, the FE circuit 16 determines the incident position of the gamma ray (the position of the scintillator 141) by computing the center-of-gravity position on the basis of the position of the photomultiplier tube 142 which converted the visible light output from the scintillator 141 into the electric signal and output the electric signal at the same timing and with the same energy.

In addition, the FE circuit 16 outputs the data created by the aforementioned process (including the detection position of the gamma ray, the energy value of the gamma ray, and the detection time of the gamma ray) to the coincidence counting circuit 17 as count information of the detector.

The coincidence counting circuit 17 creates coincidence count information using a combination of two pieces of count information obtained by approximately coincidentally counting the annihilation gamma rays emitted from the positron emitting nuclide for a predetermined time period out of the count information output from the FE circuit 16.

Specifically, the coincidence counting circuit 17 searches various kinds of digital data output from the FE circuit 16 to find a combination corresponding to an incident timing (detection time) of the gamma ray within a certain time window width (for example, 2 nanoseconds) as well as an energy value within a certain energy window width (coincidence finding). In addition, the coincidence counting circuit 17 creates coincidence count information (coincidence list) by using the output result of the found combination as information obtained by approximately coincidently counting annihilation gamma rays. In addition, the coincidence counting circuit 17 transfers the coincidence count information as projection data for the PET image reconstruction to the console 20. Here, a line connecting between two detection positions where the annihilation gamma rays are coincidently counted is called a line of response (LOR). In the present embodiment, a case where the coincidence count information is created in the gantry 10 has been described. However, the present embodiment may be applicable to a case where the coincidence count information is created in the console 20.

The console 20 is an apparatus used to receive a manipulation for the PET apparatus from an operator and reconstruct PET images (in the present embodiment, the TOF-OET images) on the basis of the coincidence count information collected by the gantry 10.

Specifically, as shown in FIG. 1, the console 20 includes an input unit 21, a display unit 22, a couch control unit 23, a calibrator 24, an image reconstruction unit 25, a data storage unit 26, and a system control unit 27. Each unit of the console 20 is connected via an internal bus.

The input unit 21 includes a mouse, a keyboard, and the like used to enter various instructions or various settings from an operator of the PET apparatus and transfers the instructions or setting information received from an operator to the system control unit 27.

The display unit 22 is a display monitor referenced by an operator and is used to display the PET images for an operator or display a graphical user interface (GUI) for receiving various instructions or various settings from an operator through the input unit 21 under control of the system control unit 27.

The couch control unit 23 controls the couch drive unit 13 to move the body of the examinee P into the scanning bore of the gantry 10.

The calibrator 24 calibrates the time information for determining the detection time of each detector module 14. The calibrator 24 will be further described in detail below.

As shown in FIG. 1, the data storage unit 26 includes coincidence count information data 26a, time information data 26b, and image data 26c. The coincidence count information data 26a store the coincidence count information created by the coincidence counting circuit 17. The image data 26c stores the PET images reconstructed by the image reconstruction unit 25. The time information data 26b store the processing result of the calibrator 24. In addition, the contents stored in the time information data 26b will be described in detail below.

The image reconstruction unit 25 reads the coincidence count information (projection data) created by the coincidence counting circuit 17 from the coincidence count information data 26a and reconstructs the PET image, for example, by successively approximating the read projection data. Furthermore, the image reconstruction unit 25 according to the present embodiment reconstructs the TOF-PET images using the time difference between the detection times of the coincidence count information. In addition, the image reconstruction unit 25 stores the reconstructed PET images in the image data 26c of the data storage unit 26.

The system control unit 27 controls the entire PET apparatus by controlling operations of the gantry 10 and the console 20. Specifically, the system control unit 27 controls the movement of the couch 12 or the process of collecting the coincidence count information by the FE circuit 16 and the coincidence counting circuit 17. In addition, the system control unit 27 controls the reconstruction process of the PET image in the image reconstruction unit 25 on the basis of the setting information entered through the input unit 21 by an operator. In addition, the system control unit 27 performs control of displaying the PET image stored in the image data 26c on the display unit 22.

Hereinbefore, the overall configuration of the PET apparatus according to the first embodiment has been described. Using such a configuration, the PET-CT apparatus according to the first embodiment reconstructs the aforementioned TOF-PET image.

Here, since the velocity of the gamma ray is a light velocity in a case where the TOF-PET image is reconstructed, time resolution of each detector module 14 of the PET apparatus is of importance. That is, in a case where the TOF-PET image is reconstructed, it is necessary to calibrate the time information for determining the detection time of each detector module 14 with high precision.

In the related art, in order to calibrate the time information, a technique of using a point radiation source including positron emitting nuclides such as germanium 68 is typically employed. In such a technique (hereinafter, referred to as a conventional technique), the point radiation source is installed within a field of view (FOV) of a PET image. For example, the point radiation source is provided in the center-of-gravity position of the scanning bore. In this state, the coincidence counting circuit 17 creates the coincidence count information. The coincidence count information includes information of the detection time of each of a pair of the detector modules 14 that detected the annihilation gamma ray as described above.

Figure 3:
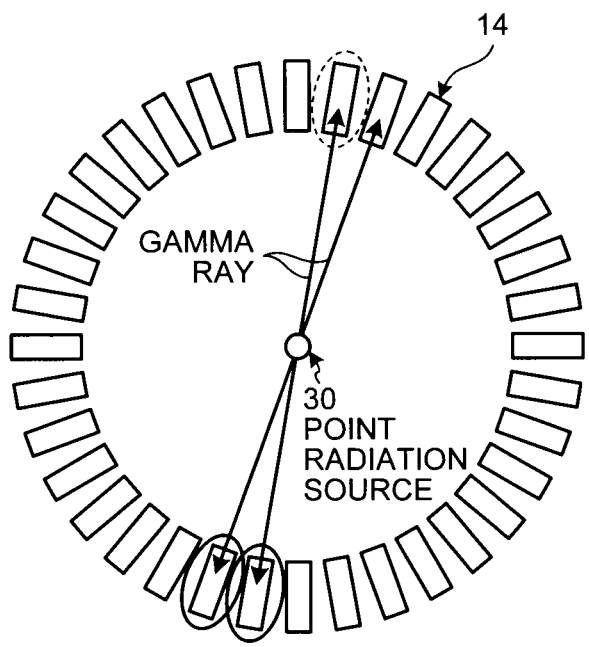
FIG. 3 is a diagram illustrating a problem with a calibration method of a related art.

In the conventional technique, the time information is calibrated by using the time difference in the detection time of each of a pair of detector modules 14 that detected the annihilation gamma rays, and the distance from the installation position of the point radiation source of each of a pair of detector modules 14. FIG. 3 is a diagram illustrating the problem with the calibration technique of the related art.

As shown in FIG. 3, in a case where a point radiation source 30 including the positron emitting nuclides is installed within the FOV, the pair of the detector modules 14 capable of detecting the annihilation gamma rays is always limited to a pair of the detector modules 14 disposed on a straight line passing the point radiation source 30. For example, in the technique of the related art, it is difficult to detect an annihilation gamma ray between one detector module 14 surrounded by a dotted-line circle of FIG. 3 and each of a pair of detector modules 14 surrounded by solid-line circles of FIG. 3. As a result, with the conventional technique, the time information of all detector modules 14 cannot be made to be adjusted.

Figure 4:
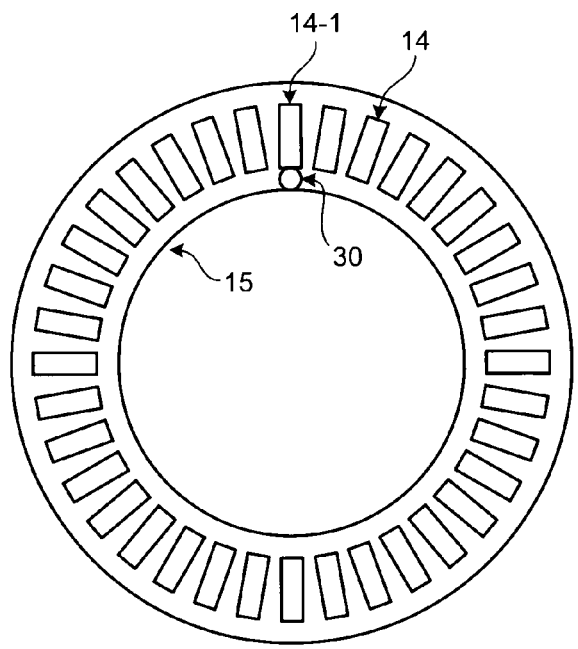
FIG. 4 is a diagram illustrating a position of a point radiation source according to the first embodiment.

In this regard, according to the present embodiment, in order to calibrate the time information of all detector modules 14, the point radiation source 30 including the positron emitting nuclide is installed in each position near a plurality of predetermined detector modules 14 within the detector cover 15 encasing the detector. FIG. 4 is a diagram illustrating an installation position of the point radiation source according to the first embodiment.

For example, as shown in FIG. 4, the point radiation source 30 is installed near a detector module 14-1 within the detector cover 15. If the point radiation source 30 is installed near the detector module 14-1, a time at which the detector module 14-1 detects one of the annihilation gamma rays emitted from the point radiation source 30 is approximately coincident with a time at which the point radiation source 30 emits the annihilation gamma rays. In addition, since the point radiation source 30 is installed near the detector module 14-1, a majority of (for example, 70%) one of the annihilation gamma rays emitted from the point radiation source 30 is incident onto the detector module 14-1. In addition, the position near the detector module 14 where the point radiation source 30 is disposed is not limited to the inside of the detector cover 15, but may be disposed on the detector cover 15.

Figure 5:
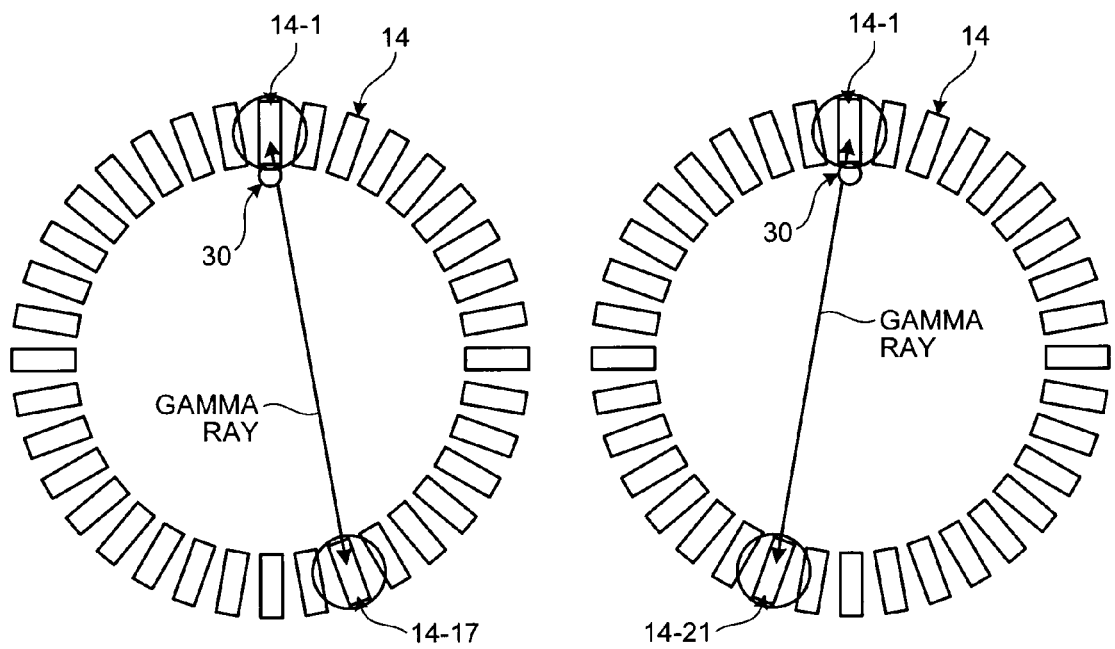
FIG. 5 is a diagram illustrating a combination of detector modules capable of detecting annihilation gamma rays according to the first embodiment.

Since the point radiation source is installed as shown in FIG. 4 according to the present embodiment, it may be possible to increase the number of combinations of the detector modules 14 capable of detecting the annihilation gamma rays in comparison with a case where the point radiation source 30 is installed within the FOV. FIG. 5 is a diagram illustrating a combination of the detector modules capable of detecting the annihilation gamma rays according to the first embodiment.

For example, as shown in FIG. 5, in the first embodiment, the annihilation gamma rays emitted from the point radiation source 30 can be detected by a combination of the detector module 14-1 and a detector module 14-17 and a combination of the detector module 14-1 and a detector module 14-21. That is, in the first embodiment, it is possible to calibrate the time information of each of a plurality of detector modules 14 using the detector module 14-1.

Here, as described above, in the first embodiment, the point radiation sources 30 are installed in a plurality of different positions near a plurality of predetermined detector modules 14. This is because, if the point radiation source 30 is installed in a single position, there is a limitation in the combinations of the detector modules 14 capable of calibrating the time information. For example, in a case where the point radiation source 30 is installed near the detector module 14-1, the precision of detection of the annihilation gamma ray of the detector module 14 near the detector module 14-1 is degraded because the incident angle of the gamma ray is reduced. That is, the calibration allowable range of the time information is limited depending on the installation location of the point radiation source 30. For example, the calibration allowable range may be set with an angle (solid angle) from the detector module 14 installed near the point radiation source 30.

Figure 6:
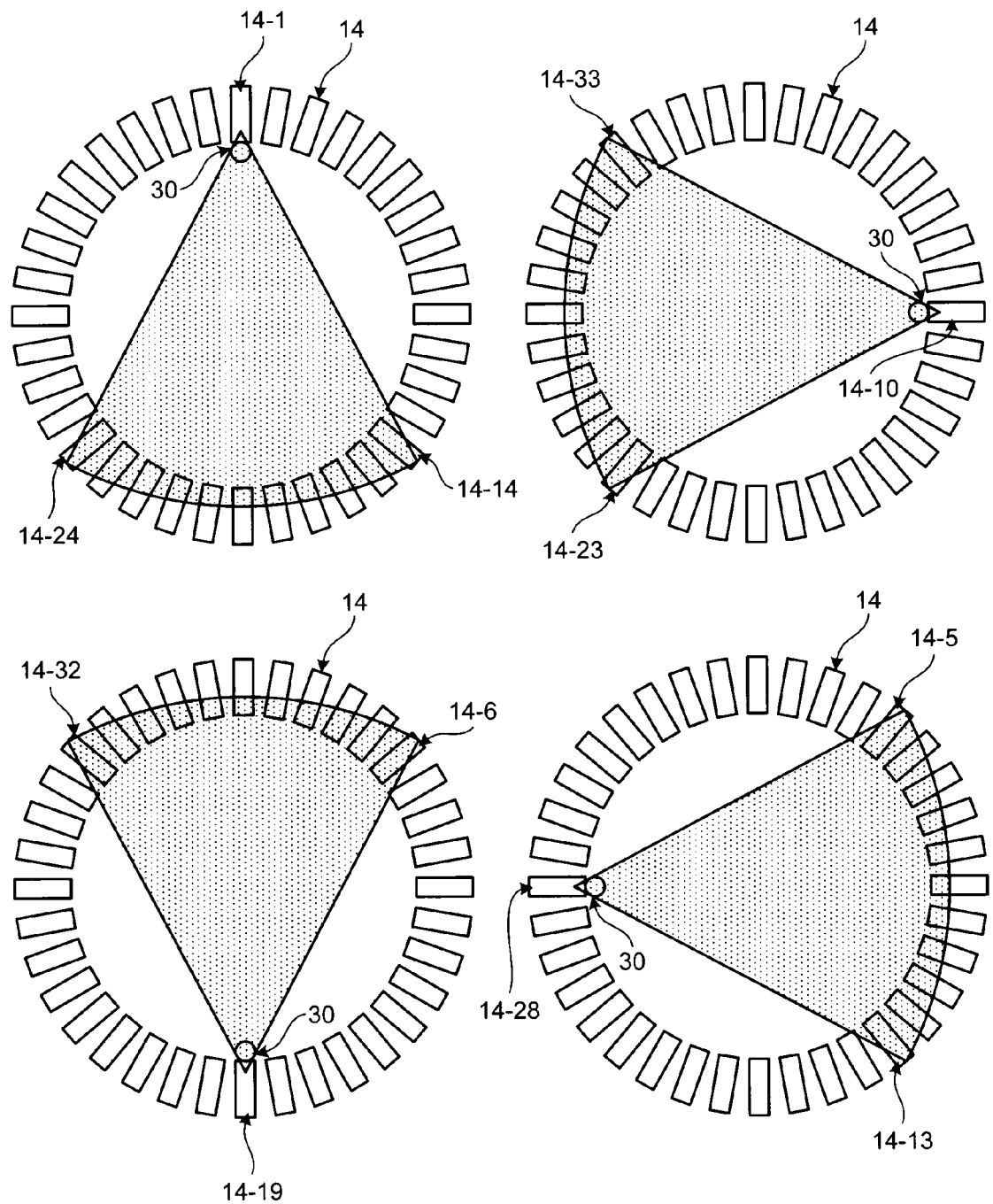
FIG. 6 is a diagram exemplarily illustrating a plurality of positions where point radiation sources are arranged according to the first embodiment.

In this regard, in the first embodiment, a plurality of installation positions of the point radiation sources 30 are adjusted such that at least one of the detector modules within the calibration allowable range established from the installation position of the point radiation source 30 is superimposed with the detector module within the calibration allowable range established from another installation position of the point radiation source 30. FIG. 6 is a diagram exemplarily illustrating a plurality of installation positions of the point radiation sources according to the first embodiment.

Figure 7:
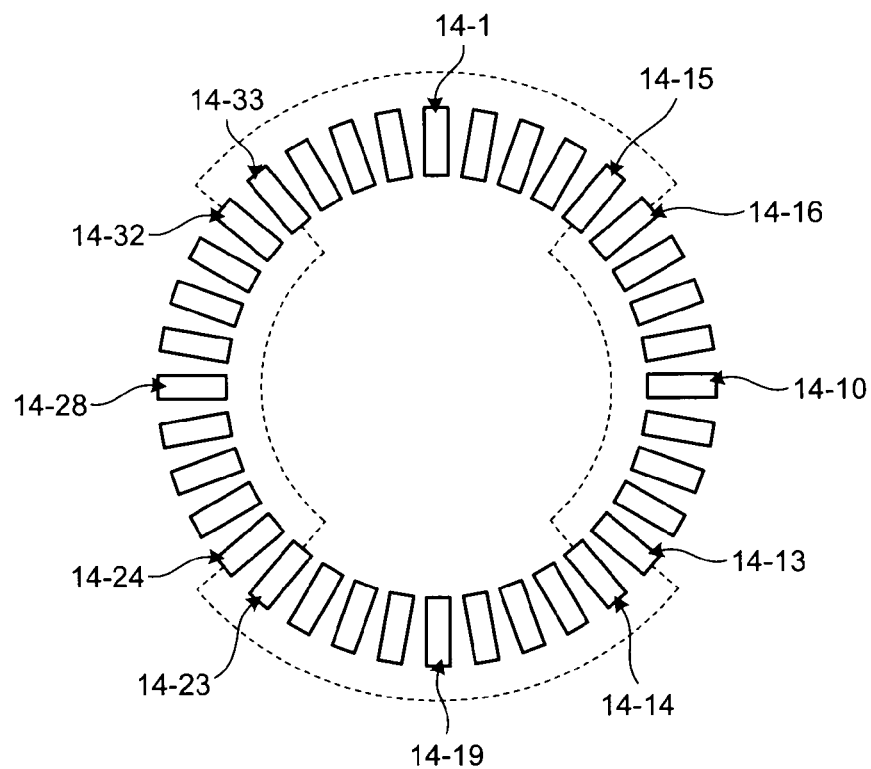
FIG. 7 is a diagram illustrating superimposition of the detector modules between the calibration allowable ranges established by the example of FIG. 6.

In the example shown in FIG. 6, the point radiation sources 30 are installed in the positions near the detector modules 14-1, 14-10, 14-19, and 14-28 (four places) out of 36 detector modules 14. As a result, in a case where the point radiation source 30 is installed in the position near the detector module 14-1, the calibration allowable range includes, for example, detector modules 14-14 to 14-24 as shown in FIG. 6. In addition, in a case where the point radiation source 30 is installed in the position near the detector module 14-10, the calibration allowable range includes, for example, detector modules 14-23 to 14-33 as shown in FIG. 6. In addition, in a case where the point radiation source 30 is installed in the position near the detector module 14-19, the calibration allowable range includes, for example, detector modules 14-32 to 14-36 and 14-1 to 14-6 as shown in FIG. 6. In addition, in a case where the point radiation source 30 is installed in the position near the detector module 14-28, the calibration allowable range includes, for example, detector modules 14-5 to 14-13 as shown in FIG. 6. FIG. 7 is a diagram illustrating superimposition of the detector modules between the calibration allowable ranges established based on the example of FIG. 6.

That is, in the example shown in FIG. 6, two detector modules 14-23 and 14-24 are superimposed in the calibration allowable range of the detector module 14-1 and the calibration allowable range of the detector module 14-10 as shown in FIG. 7. In addition, in the example shown in FIG. 6, two detector modules 14-32 and 14-33 are superimposed in the calibration allowable range of the detector module 14-10 and the calibration allowable range of the detector module 14-19 as shown in FIG. 7. In addition, in the example shown in FIG. 6, two detector modules 14-5 and 14-6 are superimposed in the calibration allowable range of the detector module 14-19 and the calibration allowable range of the detector module 14-28 as shown in FIG. 7. In addition, in the example shown in FIG. 6, two detector modules 14-13 and 14-14 are superimposed in the calibration allowable range of the detector module 14-1 and the calibration allowable range of the detector module 14-28 as shown in FIG. 7.

As a result, in the first embodiment, it is possible to calibrate the time information using all combinations of a plurality of detector modules 14. In addition, in FIGS. 3 to 7, the number of the detector modules 14 is set to 36 for the simplicity purpose in description. However, in practice, the number of the detector modules 14 provided in the PET apparatus may be set to, for example, several hundreds or more.

Figure 8A:
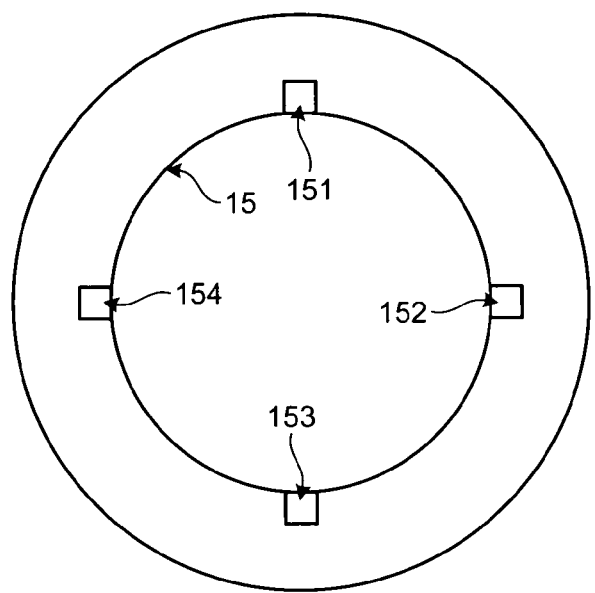
FIGS. 8A and 8B are diagrams illustrating a holder having a detector cover according to the first embodiment.
Figure 8B:
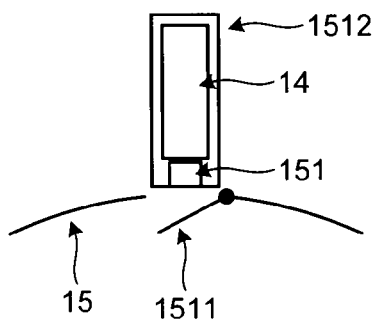

Here, the point radiation source 30 is installed within the detector cover 15 as described above. For this reason, the detector cover 15 according to the first embodiment has, for example, a holder shown in FIG. 8A or 8B in order to encase the point radiation source. FIGS. 8A and 8B are diagrams illustrating the holder provided in the detector cover according to the first embodiment.

For example, in a case where the point radiation sources 30 are installed in four places as described in the example of FIG. 6, the detector cover 15 is provided with holders 151, 152, 153, and 154 in the positions near the detector modules 14-1, 14-10, 14-19, and 14-28, respectively, as shown in FIG. 8A. As a result, it is possible to install the point radiation sources 30 adjacently.

Alternatively, the detector cover 15 is provided with, for example, doors 1511 in the positions near the detector modules 14 (detector module 14-1) as shown in FIG. 8B. In addition, the holder 151 is provided within the module cover 1512 for encasing the detector module 14-1. Similarly, doors are provided in the positions near the detector modules 14-10, 14-19, and 14-28, respectively. In addition, the holders 152, 153, and 154 are provided within the module covers for encasing the detector modules 14-10, 14-19, and 14-28, respectively. As a result, it is possible to install the point radiation sources 30 more adjacently.

Hereinbefore, a method of installing the point radiation source according to the first embodiment has been described. The process of the calibrator 24 shown in FIG. 1 is carried out while the point radiation sources 30 are installed in this manner. That is, the calibrator 24 calibrates the time information for determining the detection time of each of a pair of detector modules 14 based on each detection time of a pair of detector modules 14 which approximately coincidentally count the annihilation gamma rays from the point radiation sources 30 and the distance between the pair of detector modules 14. In addition, the calibrator 24 calibrates the time information of all of the plurality of detector modules 14.

Specifically, the calibrator 24 calibrates the time information of each of a pair of detector modules 14 which approximately coincidentally count the annihilation gamma rays from the point radiation sources 30 within a predetermined time period whenever the point radiation source 30 is sequentially installed in a plurality of different positions within the detector cover 15. For example, a manager of the PET apparatus installs the point radiation source 30 in the holder 151. Then, the manager enters a calibration measurement start request, for example, using the input unit 21. In addition, the system control unit 27 performs control to carry out the processing in the FE circuit 16 and the coincidence counting circuit 17. In order to calibrate the time information, the coincidence counting circuit 17 may create the coincidence count information by setting the time window width as a search condition. That is, the coincidence counting circuit 17 may change the search condition when a process switches between a case of the time information calibration process and a case of the image reconstruction process.

If the coincidence count information is sequentially stored in the coincidence count information data 26a in a case where the point radiation source 30 is installed in the position near the detector module 14-1, the calibrator 24 starts the process. FIG. 9 is a diagram illustrating the calibrator according to the first embodiment.

For example, it is assumed that a combination of count information detected by the detector module 14-1 (ID:1) at the time "T:t1" and count information detected by the detector module 14-14 (ID:14) at the time "T:t2" is stored in the coincidence count information data 26a as the coincidence count information as shown in FIG. 9. In FIG. 9, the reference symbol "P" denotes the detection position of the gamma ray, and the reference symbol "E" denotes the energy of the gamma ray.

In such a case, the calibrator 24 carries out the calibration process using the distance (D(1-14) of FIG. 9) between the detector modules 14-1 and 14-14. That is, the calibrator 24 computes the precise detection time "T2" of the detector module 14-14 by adding "D(1-14)/c" to the detection time "t1" of the detector module 14-1 as shown in FIG. 9. In addition, the reference symbol "c" denotes a velocity of the gamma ray, that is, a light velocity.

In addition, the calibrator 24 computes a time difference between "T2" and the detection time "t2" of detector module 14-14. The time difference computed by the calibrator 24 corresponds to an error of the time information of the detector module 14-14 with respect to the time information of the detector module 14-1. In this regard, the calibrator 24 calibrates the time information of the detector modules 14-1 and 14-14 using the computed time difference. Specifically, the calibrator 24 calibrates the time information of the detector module 14-14 by using the time information of the detector module 14-1 as a relative reference value.

As such, the calibrator 24 calibrates the time information between a pair of detector modules 14 whenever the coincidence count information combined with the count information of the detector module 14-1 is stored in the coincidence count information data 26a.

In addition, the manager of the PET apparatus sequentially installs the point radiation sources 30, for example, in order of the holders 152, 153, and 154. As a result, the calibrator 24 calibrates the time information for each of the four places. That is, the calibrator 24 calibrates the time information of the detector module 14 serving as an output source of the count information combined with the count information of the detector module 14-10 by using the time information of the detector module 14-10 as a relative reference value. In addition, the calibrator 24 calibrates the time information of the detector module 14 serving as an output source of the count information combined with the count information of the detector module 14-19 by using the time information of the detector module 14-19 as a relative reference value. In addition, the calibrator 24 calibrates the time information of the detector module 14 serving as an output source of the count information combined with the count information of the detector module 14-28 by using the time information of the detector module 14-28 as a relative reference value.

In addition, the calibrator 24 may use, for example, only the coincidence count information containing the count information of the detector module 14 within the calibration allowable range as a processing target under control of the system control unit 27 based on the settings of the manager. Alternatively, the calibrator 24 may use, for example, the coincidence count information containing the count information of the detector module 14 outside the calibration allowable range as a processing target under control of the system control unit 27 based on the settings of the manager.

As such, the calibrator 24 calibrates the time information of each detector module 14 by using the time information of the detector module 14 installed near the point radiation source 30 as the relative reference value whenever the point radiation source 30 is installed in a different position. In addition, the calibrator 24 calibrates the overall time information of a plurality of detector modules 14 when the calibration process is terminated in each installation position of the four point radiation sources 30. As describe above, a part of the detector modules 14 of which the time information can be calibrated for each installation position is superimposed in each installation position. In this regard, the calibrator 24 calibrates the time information of the detector modules 14 other than the detector module 14-1, for example, by using the time information of the detector module 14-1 as an absolute reference value (for example, "0").

For example, the calibrator 24 calibrates "the time information of each detector module 14 calibrated by using the time information of the detector module 14-10 as a relative reference value" using the difference between the time information of the detector module 14-24 calibrated by using the time information of the detector module 14-1 as a relative reference value and the time information of the detector module 14-24 calibrated by using the time information of the detector module 14-10 as a relative reference value. Similarly, the calibrator 24 calibrates the time information of each detector module 14 calibrated by using the time information of the detector module 14-19 as a relative reference value by using the time information of the detector module 14-1 as an absolute reference value. Similarly, the calibrator 24 calibrates the time information of each detector module 14 calibrated by using the time information of the detector module 14-28 as a relative reference value. As a result, the calibrator 24 determines the time information of the detector modules 14 other than the detector module 14-1 by using the time information of the detector module 14-1 as an absolute reference value.

In addition, the calibrator 24 stores the calibration results in the time information data 26b of FIG. 1. FIG. 10 is a diagram illustrating the time information data according to the first embodiment.

For example, as shown in FIG. 10, the time information data 26b stores the time information of the detector module 14 of the "ID:2" as "Δt2" in a case where the time information of the detector module 14-1(ID:1) is set to "0" as a processing result of the calibrator 24. Similarly, as shown in FIG. 10, the time information data 26b stores the time information of the detector module 14 (ID:3) as "Δt3" and the time information of the detector module 14 (ID:4) as "Δt4."

In addition, the system control unit 27 controls the reconstruction process of the image reconstruction unit 25 as described below when a scanning request for the PET image (TOF-PET image) of the subject into which a substance labeled by the positron emitting nuclide (for example, a medical agent such as 18F-labeled deoxyglucose) is introduced is received from an operator using the input unit 21.

Figure 11:
FIG. 11 is a diagram illustrating an image reconstruction unit according to the first embodiment

That is, the image reconstruction unit 25 reconstructs the TOF-PET image of the subject using the time difference between each detection time of the annihilation gamma rays corrected based on the time information of each of a plurality of detector modules 14 calibrated by the calibrator 24. FIG. 11 is a diagram illustrating the image reconstruction unit according to the first embodiment.

Specifically, the image reconstruction unit 25 corrects coincidence count information stored in the coincidence count information data 26a using the calibrated time information stored in the time information data 26b.

For example, in the example of FIG. 11, the coincidence count information for the count information "P:P1_1, E:E1_1, T:T1_1" originating from the output of the detector module 14 (ID:1) and the count information "P:P2_2, E:E2_2, T:T2_2" originating from the output of the detector module 14 (ID:2) is stored. In such a case, the image reconstruction unit 25 obtains the time information "0" of the detector module 14 (ID:1) and the time information "Δt2" of the detector module (ID:2) from the coincidence count information data 26a. In addition, the image reconstruction unit 25 does not correct "T:T1_1" but correct "T:T2_2" into "T:T2_2+Δt2" as shown in FIG. 11.

In addition, in the example of FIG. 11, the coincidence count information for the count information "P:P10_2, E:E10_2, T:T10_2" originating from the output of the detector module 14 "ID:10" and the count information "P:P3_2, E:E3_2, T:T3_2" originating from the output of the detector module 14 (ID:3) is stored. In such a case, the image reconstruction unit 25 obtains the time information "Δt10" of the detector module 14 (ID:10) and the time information "Δt3" of the detector module 14 (ID:3) from the coincidence count information data 26a. In addition, the image reconstruction unit 25 corrects "T:T10_2" into "T:T10_2+Δt10" and corrects "T:T3_2" into "T:T3_2+Δt3" as shown in FIG. 11.

In addition, in the example of FIG. 11, the coincidence count information for the count information "P:P8_3, E:E8_3, T:T8_3" originating from the output of the detector module 14 (ID:8) and the count information "P:P20_3, E:E20_3, T:T20_3" originating from the output of the detector module 14 (ID:20) is stored. In such a case, the image reconstruction unit 25 obtains the time information "Δt8" of the detector module 14 (ID:8) and the time information "Δt20" of the detector module 14 (ID:20) from the coincidence count information data 26a. In addition, the image reconstruction unit 25 corrects "T:T8_3" into "T:T8_3+Δt8" and corrects "T:T20_3" into "T:T20_3+Δt20" as shown in FIG. 11.

In addition, the image reconstruction unit 25 reconstructs the TOF-PET image using the coincidence count information obtained by correcting the detection time.

In the foregoing description, the correction process of the coincidence count information is carried out by the image reconstruction unit 25. However, the first embodiment may be similarly employed in a case where the correction process for the coincidence count information is carried out by the calibrator 24 or the system control unit 27. Alternatively, the first embodiment may be similarly employed in a case where FE circuit 16 outputs the count information obtained by correcting the detection time of each detector module 14 using the time information data 26b to the coincidence counting circuit 17 when the output data of each detector module 14 is processed. In such a case, since the detection time of the coincidence count information created by the coincidence counting circuit 17 is the data corrected based on the time information, the image reconstruction unit 25 reconstructs the TOF-PET image directly using the coincidence count information stored in the coincidence count information data 26a.

In the foregoing description, the calibrator 24 is provided in the console 20. However, the first embodiment may be similarly employed in a case where the calibrator 24 is provided in the gantry 10. Here, in a case where the FE circuit 16 corrects the detection time of each detector module 14 using the time information data 26b, the calibrator 24 is preferably provided in the gantry 10, and the time information data 26b is also preferably provided in the gantry 10. In either case, the image reconstruction unit 25 reconstructs the TOF-PET image using the coincidence count information having the detection time corrected based on the processing result of the calibrator 24.

In the first embodiment, the time information is calibrated by sequentially installing the point radiation sources 30 in a plurality of different positions. For this reason, the PET apparatus according to the present embodiment may include a pointer for instructing the installation position of the point radiation source 30 such that a manager can recognize the installation positions of the point radiation sources 30.

In the first embodiment, the point radiation sources 30 are sequentially installed in a plurality of different positions. However, the first embodiment may be similarly employed in a case where a plurality of point radiation sources 30 are installed in a plurality of different positions at once. Even in this case, it is possible to calibrate the time information of all detector modules 14. However, in order to avoid a random event from being generated as the coincidence count information, it is preferable that the point radiation sources 30 be sequentially installed in a plurality of different positions.

Figure 12:
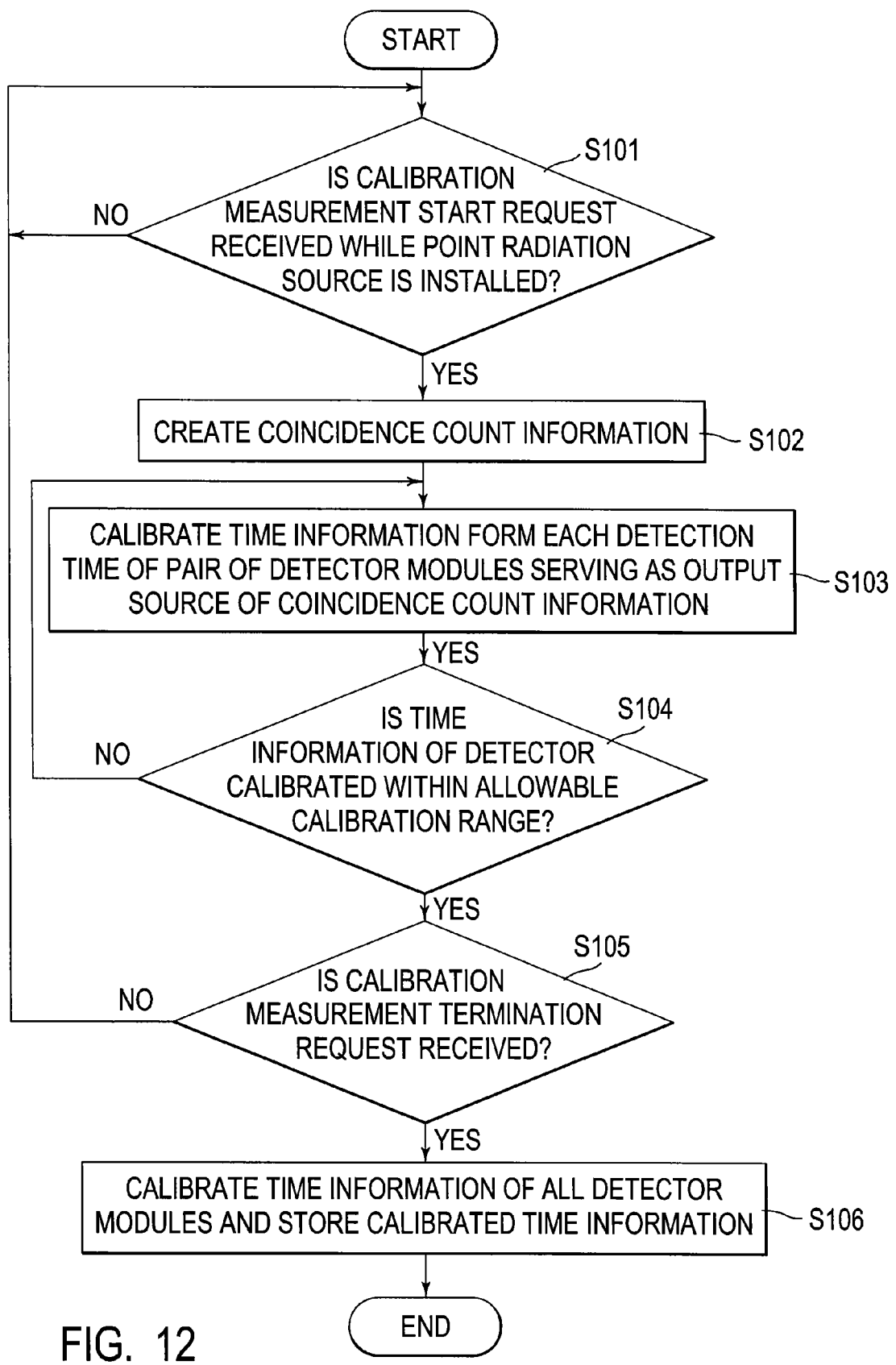
FIG. 12 is a flowchart illustrating a calibration process of the PET apparatus according to the first embodiment.
Figure 13:
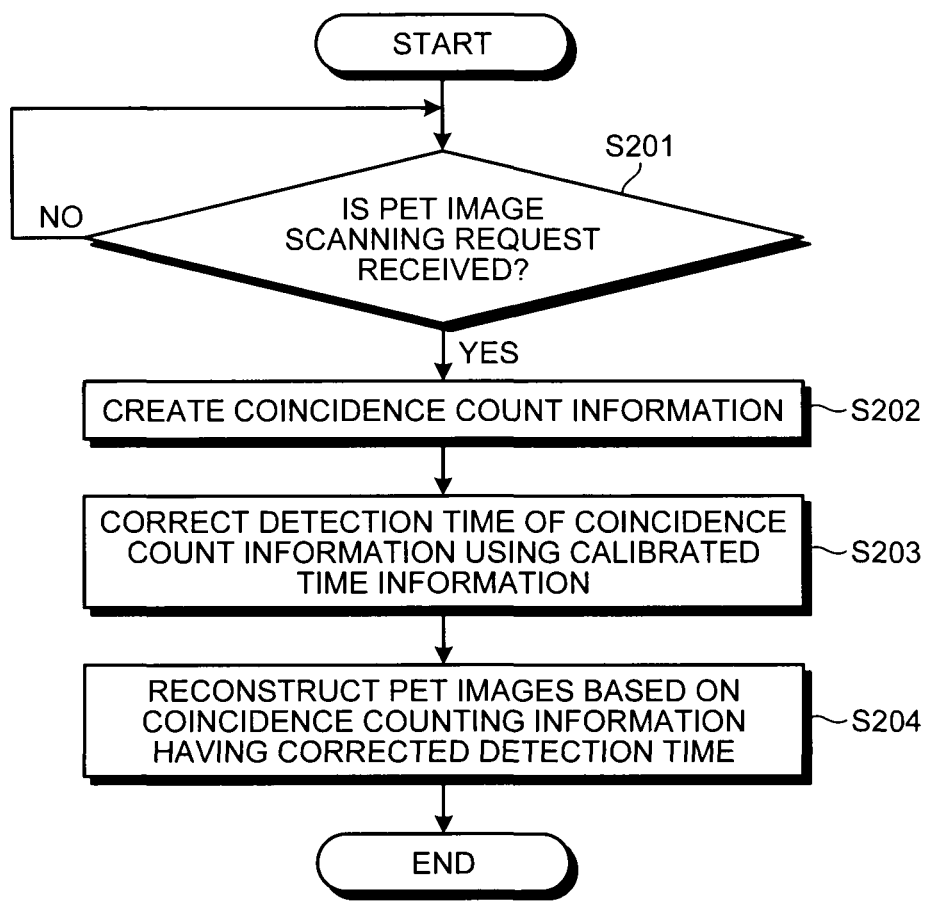
FIG. 13 is a flowchart illustrating an image reconstruction process of the PET apparatus according to the first embodiment.

Next, a flow of the processing in the PET apparatus according to the first embodiment will be described with reference to FIGS. 12 and 13. FIG. 12 is a flowchart illustrating a calibration process of the PET apparatus according to the first embodiment, and FIG. 13 is a flowchart illustrating an image reconstruction process of the PET apparatus according to the first embodiment.

As shown in FIG. 12, the PET apparatus according to the first embodiment determines whether or not the calibration measurement start request is received from a manager using the input unit 21 while the point radiation source 30 is installed (step S101). Here, if it is determined that the calibration measurement start request is not received (NO in step S101), the PET apparatus enters into a standby state.

Otherwise, if it is determined that the calibration measurement start request is received (YES in step S101), the coincidence counting circuit 17 creates the coincidence count information using the data outputted from the FE circuit 16 under control of the system control unit 27 (step S102).

In addition, the calibrator 24 calibrates the time information from each detection time of a pair of detector modules 14 serving as an output source of the coincidence count information (step S103). That is, the calibrator 24 calibrates the time information of a pair of detector modules 14 using a distance between a pair of the detector modules 14 as shown in FIG. 9.

Then, the calibrator 24 determines whether or not the time information of the detector module 14 is calibrated within the allowable calibration range (step S104). Here, if it is determined that the time information of the detector module 14 is not calibrated within the allowable calibration range (NO in step S104), the process of the calibrator 24 returns to step S103 to carry out the calibration process using the unprocessed coincidence count information.

Otherwise, if it is determined that time information of the detector module 14 is calibrated within the allowable calibration range (YES in step S104), the system control unit 27 determines whether or not the calibration measurement process termination request is received (step S105). Here, if it is determined that the calibration measurement process termination request is not received (NO in step S105), the process of the system control unit 27 returns to step S101 so that whether or not the calibration measurement start request is received is determined while the point radiation source 30 is installed in a different position.

Otherwise, if it is determined that the calibration measurement process termination request is received (YES in step S105), the calibrator 24 calibrates the time information of all detector modules 14, stores the calibrated time information in the time information data 26*b* (step S106), and terminates the process. In addition, the calibration process for the time information described above is carried out by a manager upon the shipment of the PET apparatus or during the periodic inspection of the PET apparatus.

In addition, the PET apparatus according to the first embodiment carries out the reconstruction process of the TOF-PET image using the time information data 26*b*. That is, as shown in FIG. 13, the PET apparatus according to the first embodiment determines whether or not the scanning request for the PET image (TOF-PET image) is received through the input unit 21 from an operator (step S201). Here, if it is determined that the scanning request is not received (NO in step S201), the PET apparatus enters a standby state.

Otherwise, if it is determined that the scanning request is received (YES in step S201), the coincidence counting circuit 17 creates the coincidence count information using the data outputted from the FE circuit 16 under control of the system control unit 27 (step S202).

In addition, the image reconstruction unit 25 corrects the detection time of the coincidence count information using the calibrated time information under control of the system control unit 27 (step S203, refer to FIG. 11).

Then, the image reconstruction unit 25 reconstructs the PET image (TOF-PET image) based on the coincidence count information having the corrected detection time (step S204), and terminates the process.

As described above, in the first embodiment, the calibration process for the time information is carried out while the point radiation source 30 including the positron emitting nuclide is installed in each position near a plurality of predetermined detector modules within the detector cover 15 or on the detector cover. That is, the calibrator 24 calibrates overall time information of a plurality of detector modules 14 by calibrating the time information for determining each detection time of a pair of detector modules 14 based on each detection time of a pair of detector modules 14 which approximately coincidentally count the annihilation gamma ray from the point radiation source 30 and the distance between a pair of the detector modules 14.

The image reconstruction unit 25 reconstructs the PET images of the subject using the time difference between each detection time of the annihilation gamma rays corrected based on each time information of a plurality of detector modules 14 calibrated by the calibrator 24 when the subject into which a substance labeled by the positron emitting nuclide is introduced is scanned.

Therefore, according to the first embodiment, it is possible to totally include combinations of the detector modules 14 capable of carrying out the calibration of the time information only by installing the point radiation source 30 near the detector module 14 and providing a plurality of installation positions. That is, according to the first embodiment, it is possible to conveniently calibrate the time information of all detector modules 14 with high precision. As a result, according to the first embodiment, it is possible to reconstruct the image using the detection time difference of the gamma rays with high precision.

In addition, according to the first embodiment, the calibrator 24 calibrates the time information of each of a pair of detector modules 14 which approximately coincidentally count the annihilation gamma ray whenever the point radiation sources 30 are sequentially installed within the detector cover 15 or in a plurality of different positions on the detector cover. Therefore, in the present embodiment, it is possible to avoid a random event from being generated as the coincidence count information and calibrate the time information of all detector modules 14 with high reliability.

In addition, according to the first embodiment, the installation positions of the point radiation sources 30 are adjusted such that at least one of the detector modules 14 within a calibration allowable range established from the installation position of the point radiation source 30 is superimposed on the detector module 14 within another calibration allowable range established from another installation position of the point radiation source 30. As a result, in the first embodiment, it is possible to calibrate the time information with high precision within each calibration range and calibrate the time information of all detector modules 14. Therefore, in the first embodiment, it is possible to calibrate the time information of all detector modules 14 with higher precision.

Figure 14:
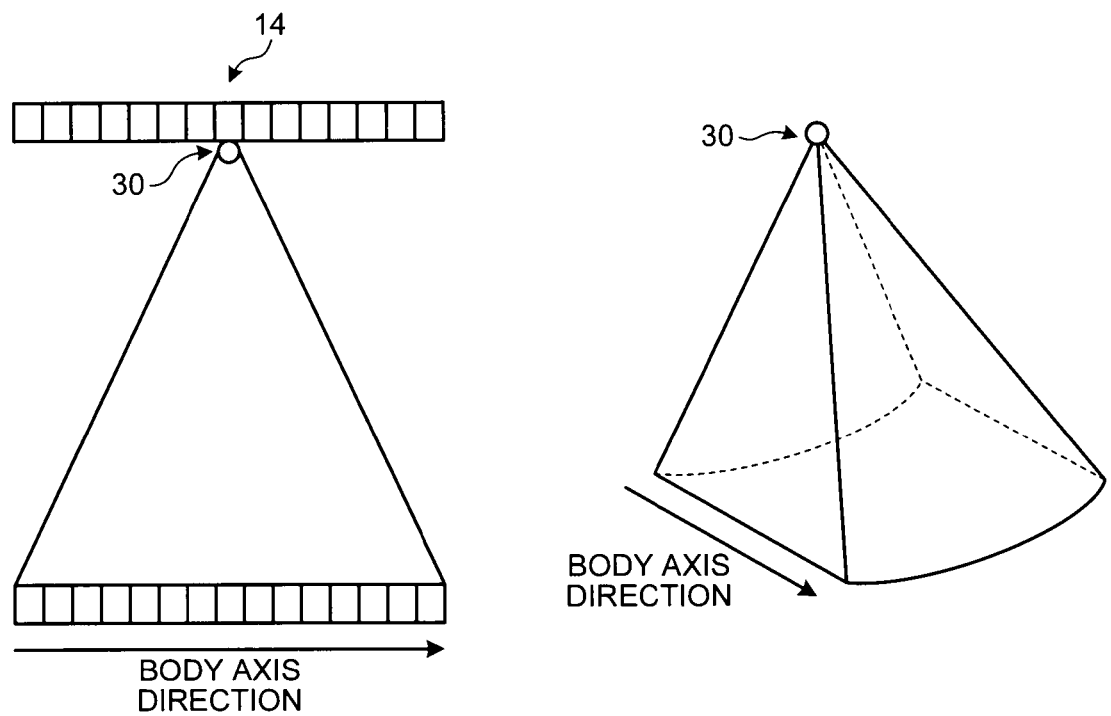
FIG. 14 is a diagram illustrating a modification of the calibration allowable range.

In the PET apparatus, a plurality of detector modules 14 arranged in a ring shape to surround the body of the examinee P are arranged in a plurality of lines along the body axis direction of the subject P, and the coincidence count information is collected three dimensionally. Even in this case, it is possible to calibrate the time information of all detector modules 14 by using the point radiation source 30 installed near the detector module 14. That is, the the first embodiment is not limited to a case where the calibration allowable range is established within a plane formed by a plurality of detector modules 14 arranged in a ring shape as described in FIG. 6. FIG. 14 is a diagram illustrating a modification of the calibration allowable range.

That is, as shown in FIG. 14, the calibration allowable range may be established in a 3-dimensional space along the body axis direction of the subject P by using the point radiation source 30 installed near the detector module 14 as a center. By establishing the calibration allowable range for each installation position of the point radiation sources 30 as shown in FIG. 14, the calibrator 24 can calibrate the time information of all detector modules 14 with high precision even when the coincidence count information is collected three dimensionally.

In the detector module 14 installed near the point radiation source 30, the count rate of the gamma rays increases. As the count rate increases, the analog waveform data are sequentially input to the FE circuit 16 during the operational process. That is, the processing target data are piled up in the FE circuit 16 so that the counting results obtained by separately counting the light components originating from respective gamma rays cannot be collected.

Figure 15:
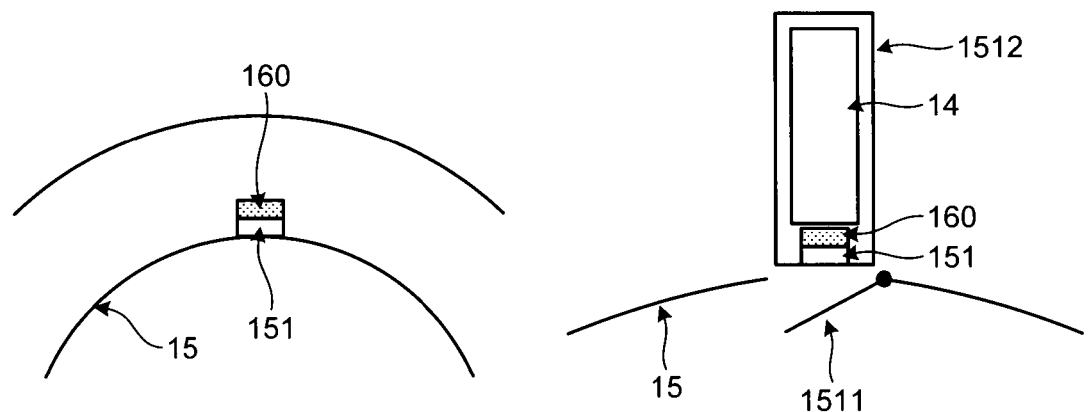
FIG. 15 is a diagram illustrating a modification of the first embodiment relating to installation of the point radiation source.

In this regard, according to the first embodiment, heavy metal may be disposed between the point radiation source 30 and the detector modules 14 near the point radiation source 30. FIG. 15 is a diagram illustrating a modification of the first embodiment relating to installation of the point radiation source.

Specifically, in the present modification, heavy metal 160 including a substance having a high density such as iron or lead is arranged in the position near the detector module 14 as shown in FIG. 15 inside each holder (refer to FIG. 8A or 8B) where the point radiation source 30 is installed. For example, in the present modification, inside the holder 151, iron is disposed, for example, with a thickness of about 3 cm. The count rate may be degraded by disposing the heavy metal 160. In the present modification, it is possible to avoid the "pile-up" and thus to efficiently collect the count results even when the point radiation source 30 is installed near the detector module 14.

In a second embodiment, a case where time information of all detector modules 14 is made to be adjusted using point radiation sources differing from those of the first embodiment will be described. In addition, a PET apparatus according to the second embodiment has a similar configuration to that of the PET apparatus of the first embodiment described with reference to FIG. 1.

According to the second embodiment, in order to make the time information of all detector modules 14 to be adjusted, a point radiation source including a positron emitting nuclide which is partially surrounded by a scatterer is installed in any position within a range surrounded by a plurality of detector modules 14 in a detector. Specifically, in the second embodiment, a point radiation source including a positron emitting nuclide of which the circumference is surrounded by a scatterer is installed. FIG. 16 is a diagram illustrating the point radiation source according to the second embodiment.

In addition, as shown in FIG. 16, a point radiation source 31 used in the second embodiment includes an object 31a having the positron emitting nuclide and a scatterer 31b that covers the circumference of the object 31a. For example, the scatterer 31b is metal having a high density. It is possible to adjust a ratio of a gamma ray emitted from the point radiation source 31 without scattering relative to a gamma ray emitted from the point radiation source 31 with scattering by adjusting the thickness of the scatterer 31b.

The point radiation source 31 in which the object 31a is covered with the scatterer 31b is installed within an FOV like the point radiation source of the related art (refer to the point radiation source 30 of FIG. 3). For example, the point radiation source 31 is installed in the center of the scanning bore. FIG. 17 is a diagram illustrating a combination of the detector modules capable of detecting the annihilation gamma rays according to the second embodiment.

Since the annihilation gamma rays emitted from the point radiation sources 31 are scattered by the scatterer 31b, they can be detected by a pair of detector modules 14 that are not present on the LOR as shown in FIG. 17. In addition, both the annihilation gamma rays emitted from the point radiation source 31 may be emitted without scattering. In this case, the annihilation gamma rays are detected by a pair of detector modules 14 on the LOR. That is, in the second embodiment, by using the point radiation source 31 having the object 31a covered with the scatterer 31b, it is possible to calibrate the time information using all combinations of the plurality of detector modules 14. In addition, the point radiation source 31 may be installed in any position within the range surrounded by the plurality of detector modules 14.

Hereinbefore, the point radiation source 31 according to the second embodiment has been described. A calibrator 24 shown in FIG. 1 carries out a process in a state in which the point radiation source 31 is installed in such a manner. That is, the calibrator 24 according to the second embodiment calibrates time information for determining a detection time of each of a pair of detector modules 14 based on each detection time of the pair of detector modules 14 which approximately coincidentally count annihilation gamma rays emitted from the point radiation source 31, on the positions of the pair of the detector modules 14, and on the position of the point radiation source 31. As a result, the calibrator 24 according to the second embodiment calibrates the overall time information of a plurality of detector modules 14.

Specifically, the calibrator 24 according to the second embodiment calibrates the time information of each of a pair of detector modules 14 which count the annihilation gamma ray from the point radiation source 31 within a predetermined time window width. First, a manager of the PET apparatus according to the second embodiment installs the point radiation source 31 and enters a calibration measurement start request using an input unit 21. In addition, a system control unit 27 performs control such that processes in an FE circuit 16 and a coincidence counting circuit 17 are carried out. For example, in a case where a calibration process for the time information is carried out, the coincidence counting circuit 17 according to the second embodiment creates coincidence count information by using only a time window width as a search condition. That is, the coincidence counting circuit 17 may change the search condition when a process switches between a case where the calibration process for the time information is carried out and a case where an image reconstruction process is carried out.

Through the aforementioned control, as the coincidence count information is sequentially stored in the coincidence count information data 26a, the calibrator 24 starts the process. FIG. 18 is a diagram illustrating the calibrator according to the second embodiment.

For example, it is assumed that a combination of the count information detected by the detector module 14 (ID:2) at the time "T:t1" and the count information detected by the detector module 14 (ID:16) at the time "T:t2" is stored in the coincidence count information data 26a as the coincidence count information as shown in FIG. 18. In addition, in FIG. 18, the reference symbol "P" denotes the detection position of the gamma ray, and the reference symbol "E" denotes the energy of the gamma ray.

In such a case, the calibrator 24 carries out the calibration process using the distance D2 between the detector module 14 (ID:2) and the point radiation source 31 and the distance D16 between the detector module 14 (ID:16) and the point radiation source 31. That is, as shown in FIG. 18, the calibrator 24 determines whether or not "t1-t2" is equal to "(D2/c)-(D16/c)." Herein, the reference symbol "c" denotes a velocity of the gamma ray, that is, a light velocity.

Here, if "t1-t2" is equal to "(D2/c)-(D16/c)," it is determined that the detection time of each of a pair of detector modules 14 (ID:2) and (ID:16) is measured by the accurate time information. However, if "t1-t2" is not equal to "(D2/c)-(D16/c)," the calibrator 24 calibrates the time information of the detector module 14 (ID:2) and the time information of the detector module 14 (ID:16). That is, the calibrator 24 calibrates the time information of the detector module 14 (ID:16), for example, by using the time information of the detector module 14 (ID:2) as a relative reference value based on the difference between "t1-t2" and "(D2/c)-(D16/c)."

In this manner, the calibrator 24 calibrates the time information between a pair of detector modules 14 whenever the coincidence count information is stored in the coincidence count information data 26a.

In addition, the calibrator 24 calibrates the time information of the detector modules 14 other than the detector module 14 (ID:1), for example, by using the time information of the detector module 14 {ID:1} as an absolute reference value (for example, "0"). As a result, the calibrator 24 calibrates the time information of all detector modules 14.

In addition, the calibrator 24 stores the result of the calibration in the time information data 26b of FIG. 1. FIG. 19 is a diagram illustrating the time information data according to the second embodiment.

For example, as shown in FIG. 19, the time information data 26b stores the time information of the detector module (ID:2) as "Δt2" assuming that the time information of the detector module 14-1(ID:1) is "0" as a processing result in the calibrator 24 according to the second embodiment. Similarly, as shown in FIG. 7, the time information data 26b stores the time information of the detector module 14 (ID:3) as "Δt3" and the time information of the detector module 14 (ID:4) as "Δt4."

In addition, the system control unit 27 controls a reconstruction process of an image reconstruction unit 25 as described below if the scanning request for the PET image (TOF-PET image) of the subject into which a substance labeled by the positron emitting nuclide (for example, a medical agent such as 18F-labeled deoxyglucose) is introduced is received from an operation through the input unit 21.

Figure 20:
FIG. 20 is a diagram illustrating an image reconstruction unit according to the second embodiment.

That is, similar to the first embodiment, the image reconstruction unit 25 reconstructs the TOF-PET image of the subject using the time difference between detection times of the annihilation gamma rays corrected based on the time information of each of a plurality of detector modules 14 calibrated by the calibrator 24. FIG. 20 is a diagram illustrating an image reconstruction unit according to the second embodiment.

Specifically, the image reconstruction unit 25 corrects the coincidence count information stored in the coincidence count information data 26a using the calibrated time information stored in the time information data 26b.

For example, in the example of FIG. 20, the coincidence count information for the count information "P:P1_1, E:E1_1, T:T_1" originating from the output of the detector module 14 (ID:1) and the count information "P:P2_2, E:E2_2, T:T2_2" originating from the output of the detector module 14 (ID:2) is stored. In such a case, the image reconstruction unit 25 obtains the time information "0" of the detector module 14 (ID:1) and the time information "Δt2" of the detector module (ID:2) from the coincidence count information data 26a. In addition, the image reconstruction unit 25 does not correct "T:T1_1" but correct "T:T2_2" into "T:T2_2+Δt2" as shown in FIG. 20.

In addition, in the example of FIG. 20, the coincidence count information for the count information "P:P10_2, E:E10_2, T:T10_2" originating from the output of the detector module 14 "ID:10" and the count information "P:P3_2, E:E3_2, T:T3_2" originating from the output of the detector module 14 (ID:3) is stored. In such a case, the image reconstruction unit 25 obtains the time information "Δt10" of the detector module 14 (ID:10) and the time information "Δt3" of the detector module 14 (ID:3) from the coincidence count information data 26a. In addition, the image reconstruction unit 25 corrects "T:T10_2" into "T:T10_2+Δt10" and corrects "T:T3_2" into "T:T3_2+Δt3" as shown in FIG. 20.

In addition, in the example of FIG. 20, the coincidence count information for the count information "P:P8_3, E:E8_3, T:T8_3" originating from the output of the detector module 14 (ID:8) and the count information "P:P20_3, E:E20_3, T:T20_3" originating from the output of the detector module 14 (ID:20) is stored. In such a case, the image reconstruction unit 25 obtains the time information "Δt8" of the detector module 14 (ID:8) and the time information "Δt20" of the detector module 14 (ID:20) from the coincidence count information data 26a. In addition, the image reconstruction unit 25 corrects "T:T8_3" into "T:T8_3+Δt8" and corrects "T:T20_3" into "T:T20_3+Δt20" as shown in FIG. 20.

In addition, the image reconstruction unit 25 reconstructs the TOF-PET image using the coincidence count information obtained by correcting the detection time.

In the foregoing description, the correction process of the coincidence count information is carried out by the image reconstruction unit 25. However, the second embodiment may be similarly employed in a case where the correction process for the coincidence count information is carried out by the calibrator 24 or the system control unit 27. Alternatively, the second embodiment may be similarly employed in a case where FE circuit 16 outputs the count information obtained by correcting the detection time of each detector module 14 using the time information data 26b to the coincidence counting circuit 17 when the output data of each detector module 14 is processed. In such a case, since the detection time of the coincidence count information created by the coincidence counting circuit 17 is the data corrected based on the time information, the image reconstruction unit 25 reconstructs the TOF-PET image directly using the coincidence count information stored in the coincidence count information data 26a.

In the foregoing description, the calibrator 24 is provided in the console 20. However, the second embodiment may be similarly employed in a case where the calibrator 24 is provided in the gantry 10. In a case where the FE circuit 16 corrects the detection time of each detector module 14 using the time information data 26b, the calibrator 24 is preferably provided in the gantry 10, and the time information data 26b is also preferably provided in the gantry 10. In either case, the image reconstruction unit 25 reconstructs the TOF-PET image using the coincidence count information having the detection time corrected based on the processing result of the calibrator 24.

Figure 21:
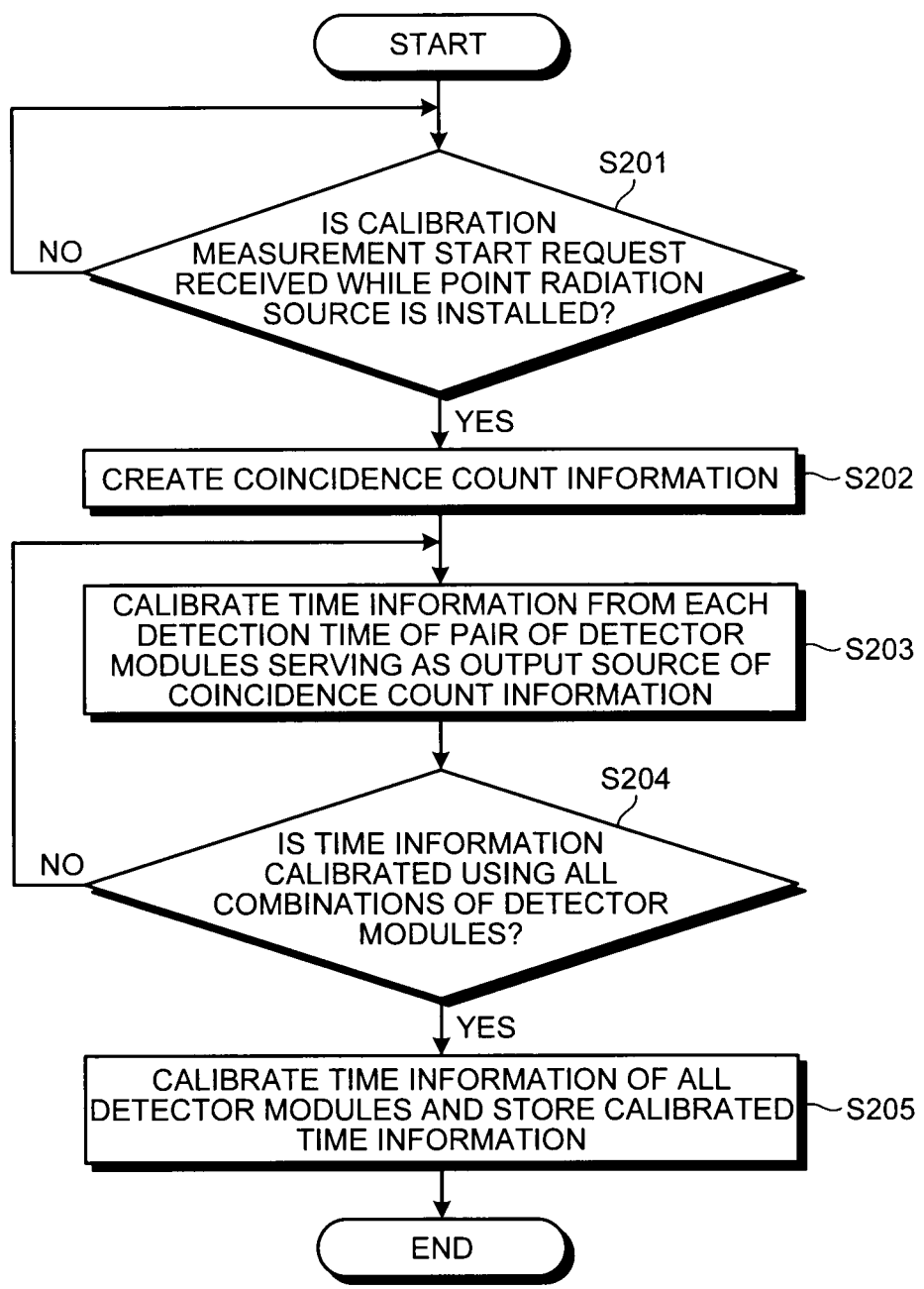
FIG. 21 is a flowchart illustrating a calibration process of the PET apparatus according to the second embodiment.
Figure 22:
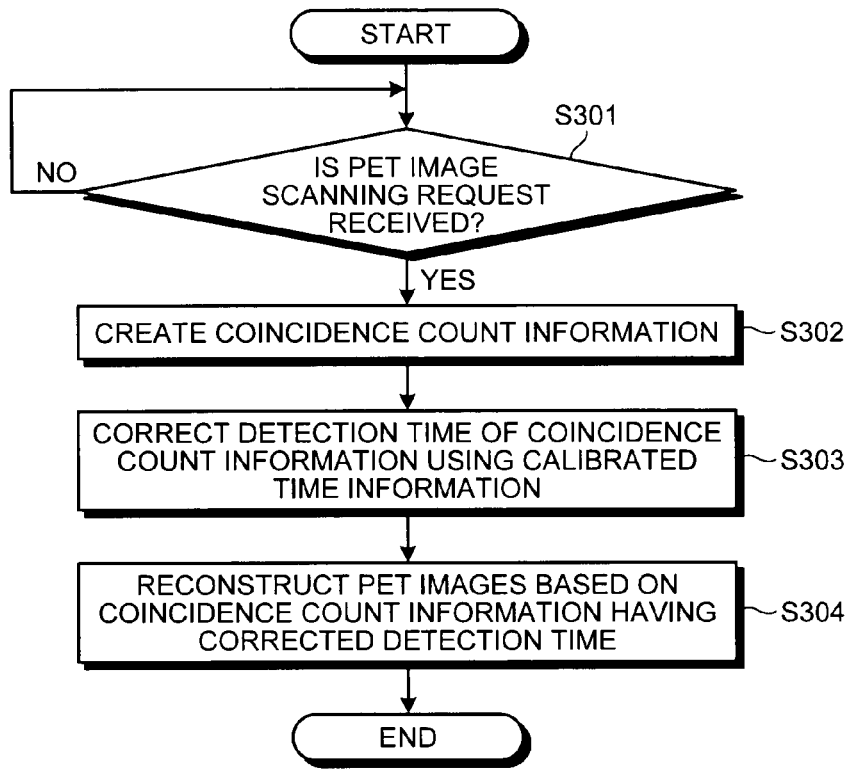
FIG. 22 is a flowchart illustrating an image reconstruction process of the PET apparatus according to the second embodiment.

Next, a flow of the processing in the PET apparatus according to the second embodiment will be described with reference to FIGS. 21 and 22. FIG. 21 is a flowchart illustrating a calibration process of the PET apparatus according to the second embodiment, and FIG. 22 is a flowchart illustrating an image reconstruction process of the PET apparatus according to the second embodiment.

As shown in FIG. 21, the PET apparatus according to the second embodiment determines whether or not the calibration measurement start request is received from a manager using the input unit 21 in a state in which the point radiation source 30 is installed (step S201). Here, if it is determined that the calibration measurement start request is not received (NO in step S201), the PET apparatus enters a standby state.

Otherwise, if it is determined that the calibration measurement start request is received (YES in step S201), the coincidence counting circuit 17 creates the coincidence count information using the data output from the FE circuit 16 under control of the system control unit 27 (step S202).

In addition, the calibrator 24 calibrates the time information from each detection time of a pair of detector modules 14 serving as an output source of the coincidence count information (step S203). That is, the calibrator 24 calibrates the time information of a pair of detector modules 14 using the distances from each of a pair of the detector modules 14 to the point radiation source 31 as shown in FIG. 18.

Then, the calibrator 24 determines whether or not the time information is calibrated using all combinations of the detector modules 14 (step S204). Here, if it is determined that the time information is not calibrated using all combinations of the detector modules 14 (NO in step S204), the process of the calibrator 24 returns to step S203 to carry out the calibration process using the unprocessed coincidence count information.

Otherwise, if it is determined that the time information is calibrated using all combinations of the detector modules (YES in step S204), the calibrator 24 calibrates the time information of all detector modules 14, stores the calibrated time information in the time information data 26b (step S205), and terminates the process. In addition, the calibration process of the time information described above may be carried out by a manager upon the shipment of the PET apparatus or during the periodic inspection of the PET apparatus.

In addition, the PET apparatus according to the second embodiment carries out the reconstruction process of the TOF-PET image using the time information data 26b. That is, as shown in FIG. 22, the PET apparatus according to the second embodiment determines whether or not the scanning request for the PET image (TOF-PET image) is received through the input unit 21 from an operator (step S301). Here, if it is determined that the scanning request is not received (NO in step S301), the PET apparatus enters a standby state.

Otherwise, if it is determined that the scanning request is received (YES in step S301), the coincidence counting circuit 17 creates the coincidence count information using the data outputted from the FE circuit 16 under control of the system control unit 27 (step S302).

In addition, the image reconstruction unit 25 corrects the detection time of the coincidence count information using the calibrated time information under control of the system control unit 27 (step S303, refer to FIG. 20).

Then, the image reconstruction unit 25 reconstructs the PET image (TOF-PET image) based on the coincidence count information having the corrected detection time (step S304), and terminates the process.

As described above, according to the second embodiment, in the detector having a plurality of detector modules 14 for counting the light originating from a gamma ray, the calibrator 24 calibrates the time information of all of a plurality of detector modules 14 by calibrating the time information for determining the detection time of each of a pair of detector modules 14 based on each detection time of the pair of detector modules 14 which approximately coincidentally count the annihilation gamma rays, the positions of the pair of detector modules 14, and the position of the point radiation source 31 in a state in which the point radiation source 31 including positron emitting nuclide, of which the circumference is surrounded by the scatterer 31b, is installed in any position within the range surrounded by a plurality of detector modules 14. The image reconstruction unit 25 reconstructs the TOF-PET image of the subject using the time difference between detection times of the annihilation gamma rays corrected based on each time information of a plurality of detector modules 14 calibrated by the calibrator 24 when the subject into which a substance labeled by the positron emitting nuclide is introduced is scanned.

Therefore, according to the second embodiment, it is possible to totally include combinations of the detector modules 14 capable of carrying out the calibration of the time information only by using the point radiation source 31 including the positron emitting nuclide of which the circumference is surrounded by the scatterer 31b. That is, according to the second embodiment, it is possible to conveniently calibrate the time information of all detector modules 14 with high precision. As a result, according to the second embodiment, it is possible to reconstruct the image using the detection time difference of the gamma rays with high precision.

Figure 23:
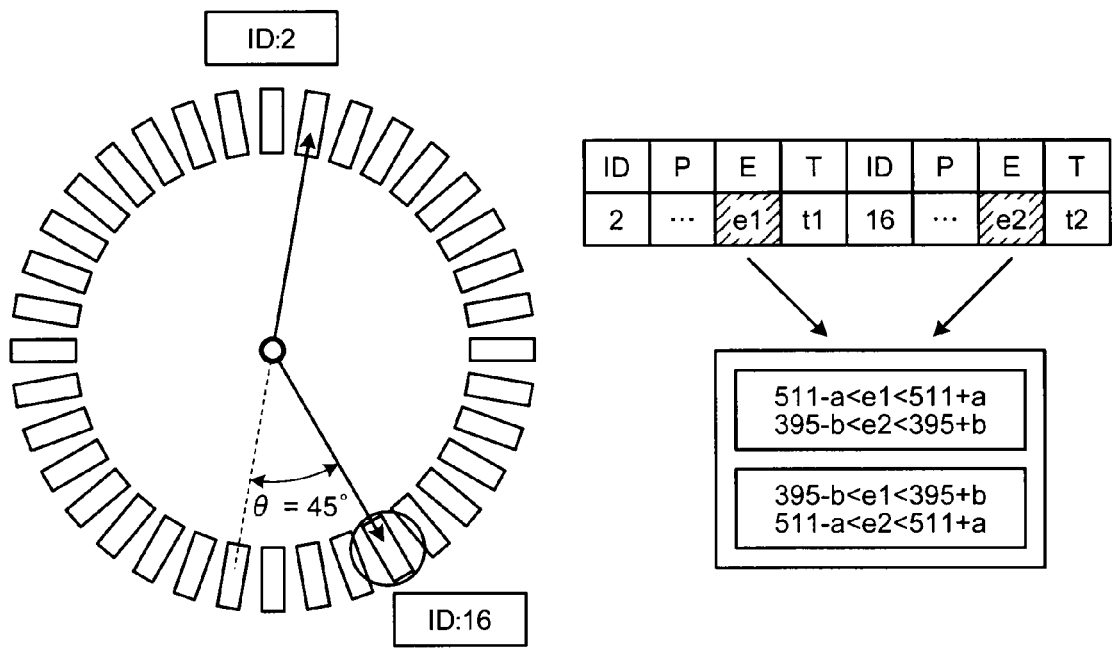
FIG. 23 is a diagram illustrating a calibrator according to a third embodiment.

In a third embodiment, a case where coincidence count information used to calibrate time information is selected will be described with reference to FIG. 23. FIG. 23 is a diagram illustrating a calibrator according to the third embodiment.

A PET apparatus according to the third embodiment is configured similar to the PET apparatus according to the second embodiment. However, a calibrator 24 calibrates the time information of each of a pair of detector modules 14 using a detection time of each of a pair of detector modules 14 which approximately coincidentally count an annihilation gamma ray, of which at least one of the gamma rays is emitted without scattering by a scatterer 31b, based on the energy of the gamma rays computed from the counting result of each detector module 14. That is, in a detector having a plurality of detector modules 14 for counting the light originating the gamma ray, the calibrator 24 according to the third embodiment specifies a pair of detector modules which approximately coincidentally count the annihilation gamma rays, of which at least one of the gamma rays is emitted without scattering by the scatterer 31b, based on the energy of the gamma rays computed from the counting results of each detector module 14 in a state in which a point radiation source 31 including a position emitting nuclide, of which the circumference is surrounded by the scatterer 31b, is installed in any position within the range surrounded by a plurality of detector modules 14. In addition, the calibrator 24 according to the third embodiment calibrates the time information for determining the detection time of each of a pair of detector modules based on each detection time of the pair of the specified detector modules 14, the positions of the pair of the specified detector modules 14, and the position of the point radiation source 31. As a result, the calibrator 24 according to the third embodiment calibrates the time information of all of a plurality of detector modules 14.

In other words, the calibrator 24 according to the third embodiment selects the coincidence count information obtained by counting the annihilation gamma rays, both with no scattering, and the coincidence count information obtained by counting the annihilation gamma rays, either one with scattering but the other one with no scattering, based on the energy of the gamma rays computed from the counting result of each detector module 14. As a result, the calibrator 24 according to the third embodiment excludes the coincidence count information obtained by detecting the annihilation gamma rays, both with scattering, from the processing target data of the time calibration.

For example, assuming that "$E_s$" denotes the energy of the gamma ray after the scattering, "$E_i$" denotes the energy of the gamma ray before the scattering (no scattering), "m" denotes an electron mass, "θ" denotes a scattering angle of the gamma ray, and "c" denotes a light velocity, the energy "$E_s$" of the gamma ray after scattering can be expressed as follows:

$$E_s = \frac{mc^2 E_i}{mc^2 + E_i(1 - \cos\theta)} \quad (1)$$

For example, using the equation (1), $E_s$ at a scattering angle of 45° becomes 395 keV when $E_i$ is set to 511 keV. That is, the gamma ray loses the energy depending on the scattering angle. Therefore, measurement precision of the counting result of the scattered rays is degraded due to the reduced energy, for example, when the detection time is measured using a threshold voltage value. For this reason, it is preferable that the detection time of the coincidence count information obtained by detecting the annihilation gamma rays both with scattering be not used to calibrate the time information.

For example, as shown in FIG. 23, for the coincidence count information, it is assumed that the energy of the count information detected by the detector module 14 (ID:2) at the time "T:t1" is set to "e1", and the energy of the count information detected by the detector module 14 (ID:16) at the time "T:t2" is set to "e2." In this regard, the calibrator 24 computes the scattering angle as "45°" from the positions of the point radiation source 31 and the pair of detector modules 14 serving as an output source of the count information for forming the coincidence count information. In addition, the calibrator 24 computes "$E_s$=365 keV" by substituting the equation (1) with "scattering angle=45°".

In addition, as shown in FIG. 23, the calibrator 24 calibrates the time information of the detector modules 14 (ID:2) and (ID:16) using the coincidence count information shown in FIG. 23 for a case of "511−a<e1<511+a" and "395−b<e2<395+b" or for a case of "395−b<e1<395+b" and "511−a<e2<511+a." That is, the calibrator 24 specifies that, for the detector modules 14 (ID:2) and (ID:16), the annihilation gamma rays, in which either one is emitted without scattering by the scatterer 31b, are approximately coincidentally counted. In addition, the calibrator 24 carries out the calibration process of the time information for the coincidence count information computed by setting the scattering angle to approximately "0°" in a case where the energy values in both sides are set to "511−a<e1<511+a." In addition, "a" and "b" shown in FIG. 23 can be arbitrarily established by a manager of the PET apparatus.

As a result, the calibrator 24 calibrates the time information of all detector modules 14 by excluding the coincidence count information obtained by detecting the annihilation gamma rays, both with scattering.

Figure 24:
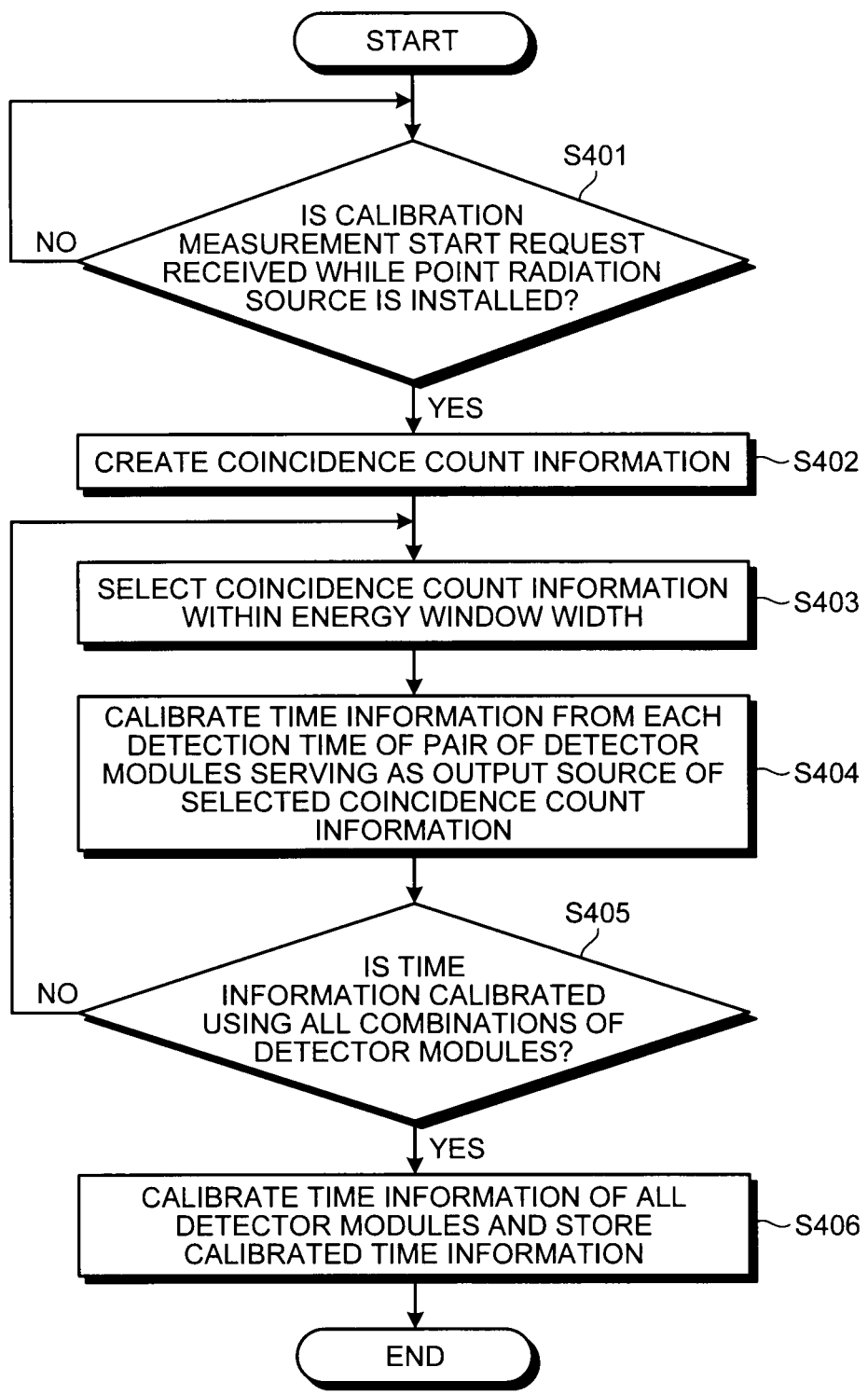
FIG. 24 is a flowchart illustrating a calibration process of a PET apparatus according to the third embodiment.

Next, a flow of the processing in the PET apparatus according to the third embodiment will be described with reference to FIG. 24. FIG. 24 is a flowchart illustrating a calibration process of the PET apparatus according to the third embodiment. In addition, an image reconstruction process of the PET apparatus according to the third embodiment is similar to the image reconstruction process of the PET apparatus according to the second embodiment described in conjunction with FIG. 22, and description thereof will not be repeated.

As shown in FIG. 24, the PET apparatus according to the third embodiment determines whether or not a calibration measurement start request is received through an input unit 21 from a manager in a state in which the point radiation source 31 is installed (step S401). Here, if it is determined that the calibration measurement start request is not received (NO in step S401), the PET apparatus enters a standby state.

Otherwise, if it is determined that the calibration measurement start request is received (YES in step S401), the coincidence counting circuit 17 creates the coincidence count information using the data output from the FE circuit 16 under control of the system control unit 27 (step S402).

In addition, the calibrator 24 selects the coincidence count information within the energy window width established by the equation (1) (step S403). That is, the calibrator 24 selects the coincidence count information obtained by counting the annihilation gamma rays both having no scattering, and the coincidence count information obtained by counting the annihilation gamma rays, either one having scattering but the other one having no scattering.

Then, the calibrator 24 calibrates the time information from each detection time of a pair of detector modules 14 serving as an output source of the selected coincidence count information (step S404).

In addition, the calibrator 24 determines whether or not the time information is calibrated using all of the combinations of the detector modules 14 (step S405). Here, if it is determined that the time information is not calibrated using all combinations of the detector modules 14 (NO in step S405), the process of the calibrator 24 returns to step S403 to carry out the calibration process using the unprocessed coincidence count information.

Otherwise, if it is determined that the time information is calibrated using all combinations of the detector modules 14 (YES in step S405), the calibrator 24 calibrates the time information of all detector modules 14, stores the calibrated time information in the time information data 26b (step S406), and terminates the process.

As described above, according to the third embodiment, since the time information of all detector modules 14 is calibrated by excluding the detection time of the coincidence count information obtained by detecting the annihilation gamma rays both having scattering, it is possible to calibrate the time information with higher precision. As a result, according to the third embodiment, it is possible to reconstruct the image using the detection time difference of the gamma rays with higher precision.

Figure 25A:
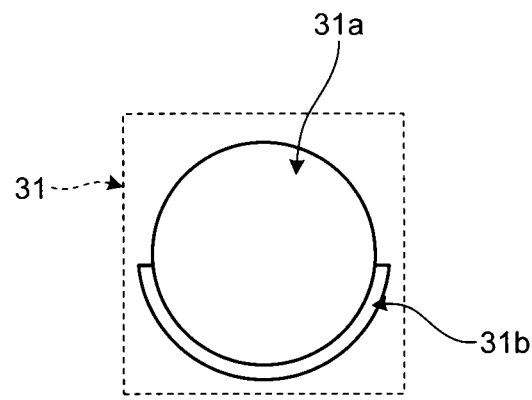
FIGS. 25A and 25B are diagrams illustrating a modification of a point radiation source used in second and third embodiments.
Figure 25B:
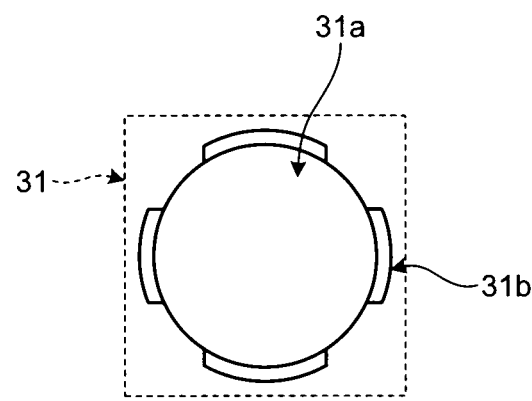

In addition, in the foregoing second and third embodiments, the point radiation source 31 is configured such that the scatterer 31b covers the entire circumference of the object 31a. Alternatively, the point radiation source 31 used in the second and third embodiments may be configured such that the scatterer 31b covers part of the object 31a. FIGS. 25A and 25B are diagrams illustrating a modification of the point radiation source used in the second and third embodiments.

For example, the point radiation source 31 may be configured such that the scatterer 31b covers a lower half part of the object 31a as shown in FIG. 25A. Alternatively, the point radiation source 31 may be configured such that the scatterer 31b covers a plurality of places of the object 31a as shown in FIG. 25B. That is, if the coincidence count information can be created using all combinations of the detector modules 14 when part of the annihilation gamma rays emitted from the point radiation source 31 scatters, the pattern for covering the object 31a using the scatterer 31b may be arbitrarily changed.

In addition, the calibrator 24 can calibrate the time information of all detector modules 14 with high precision even when the point radiation source 31 described in the second and third embodiments is used and even when the coincidence count information is collected in a 3-dimensional space.

The nuclear medicine imaging method described in the first to third embodiments may be realized by executing a prepared nuclear medicine imaging program in a computer such as a personal computer or a workstation. The nuclear medicine imaging program may be distributed via networks such as the Internet. In addition, the nuclear medicine imaging program may be recorded on a computer readable recording medium such as a hard disk, a flexible disk (FD), a compact disk-read only memory (CD-ROM), a magnetic optical disk (MO), and a digital versatile disk (DVD), and executed by being read from the recording medium using the computer.

As described above, according to the first to third embodiments, it is possible to reconstruct the image using the detection time difference of the gamma rays with high precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus comprising:
a detector including a plurality of detector modules positioned in a circular gantry, each counting light originating from a gamma ray;
a calibrator configured to calibrate time information of the plurality of detector modules based on each detection time of annihilation gamma rays emitted from a point radiation source including a positron emitting nuclide and counted approximately coincidentally by each of sets of detector modules among the plurality of detector modules, and a distance between the detector modules forming the each set of the detector modules; and
an image reconstruction unit configured to reconstruct a nuclear medicine image of a subject using a time difference between detection times of annihilation gamma rays corrected based on time information of each of the plurality of detector modules calibrated by the calibrator when the subject into which a substance labeled with a positron emitting nuclide is introduced is scanned, wherein
the each set of the detector modules includes one first detector module and at least two second detector modules, the first detector module forming the set with the at least two second detector modules,
the point radiation source is installed on the first detector module.

2. The nuclear medicine imaging apparatus according to claim 1, wherein the point radiation source is sequentially installed in a plurality of different positions of the detector.

3. The nuclear medicine imaging apparatus according to claim 2, wherein each of installed positions of the point radiation source is adjusted such that at least one of the second detector modules within a range determined from one detector module that is the first detector module corresponding to one installed position of the installed positions is superimposed on the second detector modules within a range determined from another detector module that is the first detector module corresponding to another installed position of the installed positions.

4. The nuclear medicine imaging apparatus according to claim 1, further comprising high density metal disposed between the point radiation source and the detector module near the point radiation source.

5. The nuclear medicine imaging apparatus according to claim 1, further comprising:

a cover encasing the detector, wherein the point radiation source is arranged inside the cover or on the cover.

6. The nuclear medicine imaging apparatus according to claim 5, further comprising a holder provided in the cover to receive the point radiation source.

7. A nuclear medicine imaging method comprising:
using a calibrator, calibrating time information of a plurality of detector modules positioned in a circular gantry, each of which is included in a detector and counts light originated from a gamma ray, based on each detection time of annihilation gamma rays emitted from a point radiation source including a positron emitting nuclide and counted approximately coincidentally by each set of detector modules among the plurality of detector modules, and a distance between the detector modules forming the each set of the detector modules; and
using an image reconstruction unit, reconstructing a nuclear medicine image of a subject using a time difference between each detection time of the annihilation gamma ray corrected based on time information of each of a plurality of detector modules calibrated by the calibrator when the subject into which a substance labeled by a positron emitting nuclide is introduced is scanned, wherein
the each set of the detector modules includes one first detector module and at least two second detector modules, the first detector module forming the set with the at least two second detector modules,
the point radiation source being installed on the first detector module.

8. A nuclear medicine imaging apparatus comprising:
a detector including a plurality of detector modules, each counting light originating from a gamma ray;
a calibrator configured to specify a pair of detector modules, among the plurality of detector modules, which approximately coincidentally count annihilation gamma rays, of which at least one of the annihilation gamma rays is emitted without scattering by a scatterer, based on an energy of a gamma ray computed from a counting result of each detector module while a point radiation source including a positron emitting nuclide, which is partly surrounded by the scatterer, is installed in a predetermined position within a range surrounded by the plurality of the detector modules, to collect a plurality of specified pairs of detector module, and to calibrate time information of the plurality of detector modules based on each detection time of the each specified pair of the detector modules, positions of the each specified pair of detector modules, and the predetermined position; and
an image reconstruction unit configured to reconstruct a nuclear medicine image of a subject using a time difference between each detection time of the at least one annihilation gamma ray corrected based on time information of each of the plurality of detector modules calibrated by the calibrator when the subject into which a substance labeled by a positron emitting nuclide is introduced is scanned.

9. The nuclear medicine imaging apparatus according to claim 8, wherein the calibrator is configured to use an equation for computing an energy of a scattered gamma ray from a scattering angle and an energy of a gamma ray before scattering.

10. A nuclear medicine imaging method comprising:
using a calibrator, specifying a pair of detector modules, among a plurality of detector modules each of which is included in a detector and counts light originated from a gamma ray, which approximately coincidentally count annihilation gamma rays, of which at least one of the annihilation gamma rays is emitted without scattering by a scatterer, based on an energy of a gamma ray computed from a counting result of each detector module while a point radiation source including a positron emitting nuclide, which is partly surrounded by the scatterer, is installed in a predetermined position within a range surrounded by the plurality of the detector modules, collecting a plurality of specified pairs of detector module, and calibrating time information of the plurality of detector modules based on each detection time of the each specified pair of detector modules, positions of the each specified pair of detector modules, and the predetermined position; and using an image reconstruction unit, reconstructing a nuclear medicine image of a subject using a time difference between each detection time of the at least one annihilation gamma ray corrected based on time information of each of the plurality of detector modules calibrated by the calibrator when the subject into which a substance labeled by a positron emitting nuclide is introduced is scanned.

11. The nuclear medicine imaging method according to claim 10, wherein the calibrator is configured to use an equation for computing an energy of a scattered gamma ray from a scattering angle and an energy of a gamma ray before scattering in the specifying by using the calibrator.

12. The nuclear medicine imaging apparatus according to claim 1, further comprising a detector cover encasing the plurality of detector modules, and the point radiation source installed in the detector cover, wherein a time at which the first detector module detects one of the annihilation gamma rays emitted from the point radiation source is approximately coincident with a time at which the point radiation source emits the annihilation gamma rays.

13. The nuclear medicine imaging apparatus according to claim 1, wherein a majority of one of the annihilation gamma rays emitted from the point radiation source is incident onto the first detector module.

14. The nuclear medicine imaging method according to claim 7, wherein a time at which the first detector module detects one of the annihilation gamma rays emitted from the point radiation source is approximately coincident with a time at which the point radiation source emits the annihilation gamma rays.

15. The nuclear medicine imaging method according to claim 7, wherein a majority of one of the annihilation gamma rays emitted from the point radiation source is incident onto the first detector module.

16. The nuclear medicine imaging apparatus according to claim 1, further comprising:

a module cover encasing the first detector module, wherein the point radiation source is arranged inside the module cover.

17. The nuclear medicine imaging apparatus according to claim 16, further comprising high density metal disposed between the point radiation source and the first detector module.

18. The nuclear medicine imaging apparatus according to claim 1, wherein a majority of one of the annihilation gamma rays emitting outward is incident onto the first detector module.

19. The nuclear medicine imaging apparatus according to claim 1, wherein all of one of the annihilation gamma rays emitting outward is incident onto the first detector module.

* * * * *